US007572902B2

(12) United States Patent
Abad et al.

(10) Patent No.: US 7,572,902 B2
(45) Date of Patent: Aug. 11, 2009

(54) NUCLEIC ACID MOLECULES SEQ ID NO. 16372 AND OTHER MOLECULES ASSOCIATED WITH PLANTS

(75) Inventors: Mark S. Abad, Webster Groves, MO (US); Scott E. Andersen, St. Louis, MO (US); Patrice Dubois, Richmond Heights, MO (US); Debbie A. Mahadeo, St. Louis, MO (US); James D. Masucci, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 375 days.

(21) Appl. No.: 11/330,364

(22) Filed: Jan. 12, 2006

(65) Prior Publication Data

US 2008/0276335 A1   Nov. 6, 2008

Related U.S. Application Data

(63) Continuation of application No. 09/696,664, filed on Oct. 25, 2000, now abandoned, which is a continuation-in-part of application No. 09/553,094, filed on (Continued)

(60) Provisional application No. 60/074,201, filed on Feb. 10, 1998, provisional application No. 60/074,280, filed on Feb. 10, 1998, provisional application No.

(Continued)

(51) Int. Cl.
*C07H 21/04* (2006.01)
*C12N 15/05* (2006.01)
*C12N 15/82* (2006.01)
*A01H 5/00* (2006.01)

(52) U.S. Cl. .................... 536/23.6; 800/278; 800/295; 800/298; 800/314; 800/320.3; 800/300; 800/312

(58) Field of Classification Search ............... 536/23.6; 800/278, 295, 298, 300.1, 312, 314, 320.3
See application file for complete search history.

(56) References Cited

U.S. PATENT DOCUMENTS

| 4,784,949 A | 11/1988 | Gelfand et al. |
| 4,956,282 A | 9/1990 | Goodman et al. |
| 5,011,912 A | 4/1991 | Hopp et al. |
| 6,093,545 A | 7/2000 | Goodearl et al. |

FOREIGN PATENT DOCUMENTS

WO   WO 00/18922   4/2000

OTHER PUBLICATIONS

Genseq Alignment Result 1 Jun. 3, 2004.*
AA501409, EST Database (Aug. 19, 1997).

Aach et al., "*ent*-Kaurene Biosynthesis in a Cell-Free System From Wheat (*Triticum aestivum* L.) Seedlings and the Localisation of *ent*-Kaurene Synthetase in Plastids of Three Species", *Planta* 197(2), 333-342 (1995).
Adams et al., "Complementary DNA Sequencing: Expressed Sequence Tags and Human Genome Project", *Science* 252(5013), 1651-1656 (1991).
Ait-Ali et al., "The *LS* Locus of Pea Encodes the Gibberellin Biosynthesis Enzyme *ent*-Kaurene Synthase A", *Plant J.* 11(3), 443-454 (1997).
Anaviev et al., "Oat-Maize Chromosome Addition Lines: A New System for Mapping the Maize Genome", *Proc. Natl. Acad. Sci. USA* 94, 3524-3529 (1997).
Anton et al., "Sequencing and Overexpression of the *Escherichia coli aroE* Gene Encoding Shikimate Dehydrogenase", *Biochem. J.* 249, 319-326 (1988).
Attwood, "The Babel of Bioinoformatics", *Science* 290(5491), 471-473 (2000).
Bensen et al., "Cloning and Characterization of the Maize An1 Gene", *Plant Cell* 7, 75-84.
Bentley, "The Shikimate Pathway—A Metabolic Tree with Many Branches," *Critical Rev. Biochem. Mol. Biol.* 25(5), 307-384 (1990).
Birkenbihl et al., "Cosmid-Derived Map of *E.coli* Strain BHE2600 in Comparison to the Map of Strain W3110", *Nucleic Acids Res.* 17(13), 5057-5069 (1989).
Bishop et al., "The Tomato *Dwarf* Gene Isolated by Heterologous Transposon Tagging Encodes the First Member of a New Cytochrome P450 Family", *Plant Cell* 8, 959-969 (1996).
Bonner et al., "Cloning of cDNA Encoding the Bifunctional Dehydroquinase-Shikimate Dehydrogenease of Aromatic-Amino-Acid Biosynthesis in *Nicotiana tabacum*", *Biochem J.* 362, 11-14 (1994).
Bork, "Powers and Pitfalls in Sequence Analysis: The 70% Hurdle", *Genome Res.*, 10, 398-400 (2000).
Bougri et al., "Members of a Low-Copy Number Gene Family Encoding Glutamyl-tRNA Reductase are Differentially Expressed in Barley," *Plant J.* 9(6), 867-878 (1996).
Broun et al., "Catalytic Plasticity of Fatty Acid Modification Enzymes Underlying Chemical Diversity of Plant Lipids", *Science* 282, 1315-1317 (1998).
Bukanov et al., "Ordered Cosmid Library and High-Resolution Physical-Genetic Aap of *Helicobacter pylori* Strain NCTC11638", *Mol. Microbiol.* 11(3), 509-523 (1994).

(Continued)

*Primary Examiner*—Wendy C. Haas
(74) *Attorney, Agent, or Firm*—Matthew L. Madsen; Ying-Horng Liu; Arnold & Porter LLP

(57) ABSTRACT

Expressed Sequence Tags (ESTs) isolated from maize are disclosed. The ESTs provide a unique molecular tool for the targeting and isolation of novel genes for plant protection and improvement. The disclosed ESTs have utility in the development of new strategies for understanding critical plant developmental and metabolic pathways. The disclosed ESTs have particular utility in isolating genes and promoters, identifying and mapping the genes involved in developmental and metabolic pathways, and determining gene function. Sequence homology analyses using the ESTs provided in the present invention, will result in more efficient gene screening for desirable agronomic traits. An expanding database of these select pieces of the plant genomics puzzle will quickly expand the knowledge necessary for subsequent functional validation, a key limitation in current plant biotechnology efforts.

19 Claims, No Drawings

Related U.S. Application Data

(63) Apr. 18, 2000, now abandoned, which is a continuation-in-part of application No. 09/237,183, filed on Jan. 26, 1999, which is a continuation-in-part of application No. 09/198,779, filed on Nov. 24, 1998, now abandoned, said application No. 09/237,183 is a continuation-in-part of application No. 09/227,586, filed on Jan. 8, 1999, now abandoned, said application No. 09/237,183 is a continuation-in-part of application No. 09/229,413, filed on Jan. 12, 1999, now abandoned, said application No. 09/237,183 is a continuation-in-part of application No. 09/233,218, filed on Jan. 20, 1999, now abandoned, which is a continuation-in-part of application No. 09/198,779, filed on Nov. 24, 1998, now abandoned, and a continuation-in-part of application No. 09/229,413, said application No. 09/696,664 is a continuation-in-part of application No. 09/371,146, filed on Aug. 9, 1999, now abandoned, which is a continuation-in-part of application No. 09/227,586, filed on Jan. 8, 1999, now abandoned, and a continuation-in-part of application No. 09/229,413, and a continuation-in-part of application No. 09/244,000, filed on Feb. 8, 1999, now abandoned, which is a continuation-in-part of application No. 09/198,779, said application No. 09/371,146 is a continuation-in-part of application No. 09/252,974, filed on Feb. 19, 1999, now abandoned, said application No. 09/371,146 is a continuation-in-part of application No. 09/262,979, filed on Mar. 4, 1999, now abandoned, said application No. 09/371,146 is a continuation-in-part of application No. 09/304,517, filed on May 6, 1999, now abandoned, which is a continuation-in-part of application No. 09/233,218, filed on Jan. 20, 1999, now abandoned.

(60) 60/074,281, filed on Feb. 10, 1998, provisional application No. 60/074,282, filed on Feb. 10, 1998, provisional application No. 60/074,565, filed on Feb. 12, 1998, provisional application No. 60/074,566, filed on Feb. 12, 1998, provisional application No. 60/074,567, filed on Feb. 12, 1998, provisional application No. 60/074,789, filed on Feb. 19, 1998, provisional application No. 60/075,459, filed on Feb. 19, 1998, provisional application No. 60/075,460, filed on Feb. 19, 1998, provisional application No. 60/075,461, filed on Feb. 19, 1998, provisional application No. 60/075,462, filed on Feb. 19, 1998, provisional application No. 60/075,463, filed on Feb. 19, 1998, provisional application No. 60/075,464, filed on Feb. 19, 1998, provisional application No. 60/077,229, filed on Mar. 9, 1998, provisional application No. 60/077,230, filed on Mar. 9, 1998, provisional application No. 60/078,031, filed on Mar. 16, 1998, provisional application No. 60/078,368, filed on Mar. 18, 1998, provisional application No. 60/080,844, filed on Apr. 7, 1998, provisional application No. 60/083,067, filed on Apr. 27, 1998, provisional application No. 60/083,386, filed on Apr. 29, 1998, provisional application No. 60/083,387, filed on Apr. 29, 1998, provisional application No. 60/083,388, filed on Apr. 29, 1998, provisional application No. 60/083,389, filed on Apr. 29, 1998, provisional application No. 60/084,684, filed on May 8, 1998, provisional application No. 60/085,222, filed on May 13, 1998, provisional application No. 60/085,223, filed on May 13, 1998, provisional application No. 60/085,224, filed on May 13, 1998, provisional application No. 60/085,245, filed on May 13, 1998, provisional application No. 60/086,183, filed on May 21, 1998, provisional application No. 60/086,184, filed on May 21, 1998, provisional application No. 60/086,185, filed on May 21, 1998, provisional application No. 60/086,186, filed on May 21, 1998, provisional application No. 60/086,187, filed on May 21, 1998, provisional application No. 60/086,188, filed on May 21, 1998, provisional application No. 60/086,339, filed on May 21, 1998, provisional application No. 60/089,524, filed on Jun. 16, 1998, provisional application No. 60/089,810, filed on Jun. 18, 1998, provisional application No. 60/089,814, filed on Jun. 18, 1998, provisional application No. 60/091,247, filed on Jun. 30, 1998, provisional application No. 60/092,036, filed on Jul. 8, 1998, provisional application No. 60/099,667, filed on Sep. 9, 1998, provisional application No. 60/099,668, filed on Sep. 9, 1998, provisional application No. 60/099,670, filed on Sep. 9, 1998, provisional application No. 60/099,697, filed on Sep. 9, 1998, provisional application No. 60/100,672, filed on Sep. 16, 1998, provisional application No. 60/100,673, filed on Sep. 16, 1998, provisional application No. 60/100,674, filed on Sep. 16, 1998, provisional application No. 60/101,130, filed on Sep. 21, 1998, provisional application No. 60/101,132, filed on Sep. 21, 1998, provisional application No. 60/108,996, filed on Nov. 18, 1998, provisional application No. 60/109,018, filed on Nov. 19, 1998, provisional application No. 60/071,064, filed on Jan. 9, 1998, provisional application No. 60/085,533, filed on May 15, 1998 provisional application No. 60/089,806, filed on Jun. 18, 1998, provisional application No. 60/089,807, filed on Jun. 18, 1998, provisional application No. 60/089,808, filed on Jun. 18, 1998, provisional application No. 60/089,811, filed on Jun. 18, 1998, provisional application No. 60/089,812, filed on Jun. 18, 1998, provisional application No. 60/089,813, filed on Jun. 18, 1998, provisional application No. 60/091,405, filed on Jun. 30, 1998, provisional application No. 60/099,697, filed on Sep. 9, 1998, provisional application No. 60/100,963, filed on Sep. 17, 1998, provisional application No. 60/101,343, filed on Sep. 22, 1998, provisional application No. 60/101,344, filed on Sep. 22, 1998, provisional application No. 60/101,347, filed on Sep. 22, 1998, provisional application No. 60/101,508, filed on Sep. 22, 1998, provisional application No. 60/101,707, filed on Sep. 25, 1998, provisional application No. 60/104,124, filed on Oct. 13, 1998, provisional application No. 60/104,126, filed on Oct. 13, 1998, provisional application No. 60/104,127, filed on Oct. 13, 1998, provisional application No. 60/104,128, filed on Oct. 13, 1998, provisional application No. 60/111,981, filed on Dec. 11, 1998, provisional application No. 60/072,027, filed on Jan. 21, 1998, provisional application No. 60/072,888, filed on Jan. 27, 1998, provisional application No. 60/076,709, filed on Jun. 9, 1998, provisional application No. 60/076,912, filed on Mar. 6, 1998, provisional application No. 60/083,390, filed on Apr. 29, 1998, provisional application No. 60/085,057, filed on May 12, 1998, provisional application No. 60/085,429, filed on May 14, 1998, provisional application No. 60/085,245, filed on May 13, 1998, provisional application No. 60/085,940, filed on May 19, 1998, provisional application No. 60/086,594, filed on May 22, 1998, provisional application No. 60/086,608, filed on May 22, 1998, provisional application No. 60/087,422, filed on Jun. 1, 1998, provisional application No. 60/087,631, filed on Jun. 2, 1998, provisional application No. 60/087,762, filed on Jun. 2, 1998, provisional application No. 60/087,972, filed on Jun. 4, 1998, provisional application No. 60/087,973, filed on Jun. 4, 1998, provisional application No. 60/088,441, filed on Jun. 8, 1998, provisional application No. 60/089,627, filed on Jun. 16, 1998, provisional application No. 60/089,789, filed on Jun. 18, 1998, provisional application No. 60/090,170, filed on Jun. 22, 1998, provisional application No. 60/090,856, filed on Jun. 26, 1998, provisional application No. 60/090,928, filed on Jun. 26, 1998, provisional application No. 60/091,035, filed on Jun. 29, 1998, provisional application No. 60/091,247, filed on Jun. 30, 1998, provisional application No. 60/092,036, filed on Jul. 8, 1998, provisional application No. 60/110,108, filed on Nov. 25, 1998, provisional application No. 60/110,109, filed on Nov. 25, 1998, provisional application No. 60/111,033, filed on Dec. 4, 1998, provisional application No. 60/111,742, filed on Dec. 10, 1998, provisional application No. 60/069,472, filed on Dec. 9, 1997, provisional application No. 60/077,231, filed on Mar. 9, 1998, provisional application No. 60/071,479, filed on Jan. 13, 1998.

(56) References Cited

OTHER PUBLICATIONS

Charles et al., "Isolation, Characterization and Nucleotide Sequences of the aroC Genes encoding Chorismate Synthase from *Salmonella typhi* and *Escherichia coli*", *J. Gen. Microbiol.* 136, 353-358 (1990).
Chen et al., "Microcolinearity in *sh2*-Homologous Regions of the Maize, Rice, and Sorghum Genomes", *Proc. Natl. Acad. Sci. USA* 94, 3431-3435 (1997).
Coulson et al., "Toward a Physical Map of the Genome of the Nematode *Caenorhabditis elegans*", *Proc. Natl. Acad. Sci. USA* 83, 7821-7825 (1986).
Day et al., "Cloning of the cDNA for Glutamyl-tRNA Synthetase from *Arabidopsis thaliana*", *Biochim. Biophys. Acta* 1399(2-3):219-224 (1998).
Duncan et al., "The Overexpression and Complete Amino Acid Sequence of *Escherichia coli* 3-Dehydroquinase", *Biochem. J.* 238, 475-483 (1986).
Eberhard et al., "Cloning and Expression in Yeast of a Higher Plant Chorismate Mutase", *FEBS Lett.* 334(2), 233-236 (1993).
Ebert et al., "Identification of an Essential Upstream Element in the Nopaline Synthase Promoter by Stable and Transient Assays", *Proc. Natl. Acad. Sci. USA* 84(16), 5745-5749 (1987).
Efstratiadis et al., "Enzymatic in Vitro Synthesis of Globin Genes", *Cell* 7, 279-288 (1976).
Eiglmeier et al., "Use of an Ordered Cosmid Library to Deduce the Genomic Organization of *Mycobacterium leprae*", *Mol. Microbiol.* 7(2), 197-206 (1993).
Evans et al., "Immunodetection of Recombinant Proteins Based on Antibodies Directed Against a Metal Binding Peptide Engineered for Purification by Immobilized Metal Affinity Chromatography," *J. Immunol. Meth.* 156(2), 231-238 (1992) (Abstract Only).
Entrez Accession No. M21071 J03227 (Sep. 15, 1989).
Entrez Accession No. 170374 (Sep. 15, 1989).
Entrez Accession No. M27715 (Jun. 15, 1990).
Entrez Accession No. 153878 (Jun. 15, 1990).
Entrez Accession No. X59509 S55160 (Jun. 30, 1993).
Entrez Accession No. 48906 (Jun. 30, 1993).
Entrez Accession No. Y00710 (Sep. 12, 1993).
Entrez Accession No. 40978 (Sep. 12, 1993).
Entrez Accession No. Z26519 (Dec. 2, 1993).
Entrez Accession No. 429153 (Dec. 2, 1993).
Entrez Accession No. 551666 (Jan. 25, 1995).
Entrez Accession No. X81413 (Jan. 25, 1995).
Entrez Accession No. M87280 M99707 (Apr. 12, 1995).
Entrez Accession No. 551855 (Apr. 12, 1995).
Entrez Accession No. 313150 (Jun. 13, 1995).
Entrez Accession No. X73535 (Jun. 13, 1995).
Entrez Accession No. X04306 (Jul. 12, 1995).
Entrez Accession No. 40973 (Jul. 12, 1995).
Entrez Accession No. D63474 D16312 (Jul. 27, 1995).
Entrez Accession No. 474964 (Jul. 27, 1995).
Entrez Accession No. 987267 (Jul. 31, 1995).
Entrez Accession No. U32579 (Sep. 16, 1995).
Entrez Accession No. X82831 (Mar. 1, 1996).
Entrez Accession No. 1213067 (Mar. 1, 1996).
Entrez Accession No. 1220402 (Mar. 5, 1996).
Entrez Accession No. M63245 (Mar. 11, 1996).
Entrez Accession No. W49458 (May 28, 1996).
Entrez Accession No. 1421741 (Oct. 17, 1996).
Entrez Accession No. U54770 (Oct. 18, 1996).
Entrez Accession No. X86101 (Nov. 8, 1996).
Entrez Accession No. 520943 (Feb. 26, 1997).
Entrez Accession No. 2160544 (Jun. 5, 1997).
Entrez Accession No. U63652 (Jun. 6, 1997).
Entrez Accession No. 2257714 (Jul. 15, 1997).
Entrez Accession No. U93215 (Jul. 15, 1997).
Entrez Accession No. 2224890 (Jul. 31, 1997).
Entrez Accession No. 2224892 (Jul. 31, 1997).
Entrez Accession No. U61385 (Aug. 1, 1997).
Entrez Accession No. U61386 (Aug. 1, 1997).
Entrez Accession No. 2316104 (Aug. 8, 1997).
Entrez Accession No. AF010169 (Aug. 9, 1997).
Entrez Accession No. 1524045 (Aug. 20, 1997).
Entrez Accession No. X96943 (Aug. 20, 1997).
Entrez Accession No. Y12809 (Dec. 2, 1997).
Entrez Accession No. D88382 (Mar. 17, 1998).
Entrez Accession No. 3068709 (Apr. 2, 1998).
Entrez Accession No. AF058763 (Aug. 16, 1998).
Entrez Accession No. 3420233 (Apr. 20, 1998).
Entrez Accession No. AF049236 (Apr. 22, 1998).
Entrez Accession No. AF038152 (May 7, 1998).
Entrez Accession No. 2708690 (May 7, 1998).
Entrez Accession No. AC003058 (May 16, 1998).
Entrez Accession No. 3135277 (May 16, 1998).
Entrez Accession No. 3288821 (Jul. 20, 1998).
Entrez Accession No. AF063901 (Jul. 21, 1998).
Entrez Accession No. 3435196 (Sep. 21, 1998).
Entrez Accession No. AF067773 (Sep. 22, 1998).
Entrez Accession No. 3694811 (Sep. 24, 1998).
Entrez Accession No. AJ225107 (Oct. 1, 1998).
Entrez Accession No. 3093410 (Oct. 1, 1998).
Entrez Accession No. AF060481 (Oct. 4, 1998).
Entrez Accession No. 3925407 (Nov. 24, 1998).
Entrez Accession No. AF083948 (Nov. 25, 1998).
Entrez Accession No. AB015492 (Dec. 11, 1998).
Entrez Accession No. 4001680 (Dec. 11, 1998).
Entrez Accession No. AF017431 (Jan. 2, 1999).
Entrez Accession No. 3080490 (Jan. 12, 1999).
Entrez Accession No. AL022602 (Jan. 12, 1999).
Entrez Accession No. AB011416 (Feb. 5, 1999).
Entrez Accession No. AAC17095 GI:315616 (Apr. 5, 1999).
Entrez Accession No. AP000836; GI:6539551 (Aug. 12, 2000).
Entrez Accession No. AY013245 (May 7, 2002).
Fiedler et al., "The Formation of Homogentisate in the Biosynthesis of Tocopherol and Plastoquinone in Spinach Chloroplasts", *Planta* 155, 511-515 (1982).
Garbe et al., "The *Mycobacterium tuberculosis* Shikimate Pathway Genes: Evolutionary Relationship Between Biosynthetic and Catabolic 3-Dehydroquinases", *Mol. Gen. Genet.* 228, 385-392 (1991).

Gasser et al., "Structure, Expression, and Evolution of the 5-Enolpyruvylshikimate-3-Phosphate Synthase Genes of Petunia and Tomato", *J. Biol. Chem.* 263, 4280-4289 (1988).
Gaubier et al., "A Chlorophyll Synthetase Gene from *Arabidopsis thaliana*", *Mol. Gen. Genet.* 249, 58-64 (1995).
GenBank Accession No. U03774 (Jun. 22, 1994).
GenBank Accession No. L37750 (Aug. 3, 1995).
GenBank Accession No. H30177 (Aug. 16, 1995).
GenBank Accession No. W21756 (May 6, 1996).
GenBank Accession No. X80265 (Feb. 26, 1997).
GenBank Accession No. E03435 (Sep. 29, 1997).
GenBank Accession No. AF015462 (Jul. 16, 1998).
Genbank Accession No. AC005922 (Nov. 14, 1998).
GenBank Accession No. X74737 (Jan. 21, 1999).
GenBank Accession No. AU033328 (Apr. 28, 1999).
GenBank Accession No. AQ402486 (Mar. 13, 1999).
GenBank Accession No. AI861202 (Jul. 19, 1999).
GenBank Accession No. AC018632 (Dec. 15, 1999).
GenBank Accession No. AI834598 (Feb. 2, 2000).
GenBank Accession No. AZ134591 (Jun. 2, 2000).
GenBank Accession No. BE428765 (Jul. 26, 2000).
GenBank Accession No. BF542512 (Dec. 11, 2000).
GenBank Accession No. AW871780 (Dec. 11, 2001).
GenBank Accession No. BQ603510 (Jun. 24, 2002).
GenBank Accession No. DR37H4T (Nov. 22, 2002).
GenBank Accession No. BX513761 (May 27, 2003).
GenEMBL Accession No. AF096555 (Jul. 22, 1999).
GenEMBL Accession No. AL096768 (Dec. 12, 1999).
GenSeq Accession No. AAZ35275 (Mar. 27, 2000).
Gerhold et al., "It's the genes! EST access to human genome content", *BioEssays* 18(2), 973-981 (1996).
Gibson et al., "The Bacteriochlorophyll Biosynthesis Gene, bchM, of *Rhodobacter sphaeroides* Encodes S-Adenosyl-1-Methionine: Mg Protoporphyrin IX Methyltransferase", *FEBS Lett.* 352, 127-130 (1994).
Goers et al., "The Differential Allosteric Regulation of Two Chorismate-Mutase Isoenzymes of *Nicotiana silvestris*", *Planta* 162, 117-124 (1984).
Goff, "Rice as a Model for Cereal Genomics", *Curr. Opin. Plant Biol.* 2, 86-89 (1999).
Hedden et al., "Gibberellin Biosynthesis: Enzymes, Genes and Their Regulation", *Annu. Rev. Plant Physiol. Plant Mol. Biol.* 48, 431-460 (1997).
Herrmann, "The Shikimate Pathway as an Entry to Aromatic Secondary Metabolism," *Plant Physiol.* 107, 7-12 (1995).
Hong, "A Rapid and Accurate Strategy for Rice Contig Map Construction by Combination of Fingerprinting and Hybridization", *Plant Mol. Biol.* 35,129-133 (1997).
Hundle et al., "Functional Assignment of *Erwinia herbicola* Eho10 Carotenoid Genes Expressed in *Escherichia coli*", *Mol. Gen. Genet.* 245, 406-416 (1994).
Ibba, "Biochemistry and Bioinformatics: When Worlds Collide," *Trends in Biochem. Sci.* 27(2), 64 (2000).
Iyer et al., "*Quod erat demonstrandum*! The Mystery of Experimental Validation of Apparently Erroneous Computational Analysis of Protein Aequences", *Genome Biol.* 2(12), 1-11 (2001).
Johnston et al., "Cloning and Characterization of Potato cDNAs Involved in Tetrapyrrole Biosynthesis: Ferrochelatase (Accession No. AJ005802), Chloroplatic Protoporphyrinogen IX Oxidase (Accession No. AJ225107), and Mitochondrial Protoporphyrinogen IX Oxidase (Accession No. AJ225108)", *Plant Physiol.* 118, 329-331 (1998).
Keon et al., "Isolation and Heterologous Expression of a Gene Encoding 4-Hydroxyphenylpyruvate Dioxygenase from the Wheat Leaf-Spot Pathogen, *Mycosphaerella graminicola*", *FEMS Microbiol. Lett.* 161, 337-343 (1998).
Kidwell et al., "Transposable Elements as Sources of Variation in Animals and Plants", *Proc. Natl. Acad. Sci. USA* 94, 7704-7711 (1997).
Kim et al., "Construction and Characterization of a Human Bacterial Artificial Chromosome Library", *Genomics* 34, 213-218 (1996).

Knott et al., "Randomly Picked Cosmid Clones Overlap the *pyrB* and *oriC* gap in the Physical Map of the *E.coli* Chromosome", *Nucleic Acids Res.* 16, 2601-2612 (1988).
Ko et al., "An 'Equalized cDNA' Library by the Reassociation of Short Double-Stranded cDNAs", *Nucleic Acids Res.* 18(19), 5705-5711 (1990).
Kyrpides et al., "Whole-Genome Sequence Annotation: 'Going Wrong With Confidence'", *Mol. Microbiol.* 32, 886-887 (1999).
Kurata et al., "A 300 Kilobase Interval Genetic Map of Rice Including 883 Expressed Sequences," *Nature Gen.* 8(4), 362-372 (1994).
Lange et al., "Cloning and Expression of Gibberellin 2β,3β-Hydroxylase cDNA from Pumpkin Endosperm," *Plant Cell* 9(8), 1459-1467 (1997).
Lange "Cloning Gibberellin Dioxygenase Genes from Pumpkin Endosperm by Heterologous Expression of Enzyme Activities in *Escherichia coli*", *Proc. Natl. Acad. Sci. USA* 94(12), 6553-6558 (1997).
Lange et al., "Expression Cloning of a Gibberellin 20-Oxidase, a Multifunctional Enzyme Involved in Gibberellin Biosynthesis", *Proc. Natl. Acad. Sci. USA* 91(18), 8552-8556 (1994).
Liepman et al., "Sequence Analysis of a cDNA Encoding Alanine:Glyoxylate Amino Transferase from *Arabidopsis* (Accession No. AF063901)", *Plant Physiol.* 117, 1125-1127 (1998).
Lim et al., "Porphobilinogen Deaminase is Encoded by a Single Gene in *Arabidopsis thaliana* and Is Targeted to the Chloroplasts," *Plant Mol. Biol.* 26, 863-872 (1994).
Mahairas et al., "Sequence-Tagged Connectors: A Sequence Approach to Mapping and Scanning the Human Genome", *Proc. Natl. Acad. Sci. USA* 96, 9739-9744 (1999).
Martin et al., "MYB Transcription Factors in Plants", *Trends Genet.* 13(2), 67-73 (1997).
Martin et al., "Mendel's Dwarfing Gene: cDNAs from the *Le* Alleles and Function of the Expressed Proteins", *Proc. Natl. Acad. Sci. USA*, 94(16):8907-8911 (1997).
McCombie et al., "*Caenorhabditis elegans* Expressed Sequence Tags Identify Gene Families and Disease Gene Homologues," *Nature Gen.* 1, 124-131 (1992).
Meinkoth et al., "Hybridization of Nucleic Acids Immobilized on Solid Supports", *Anal. Biochem.* 138, 267-284 (1984).
Mende et al., "The Geranylgeranyl Diphosphate Synthase Gene of *Gibberella fujikuroi*: Isolation and Expression", *Mol. Gen. Genet.* 255(1), 96-105 (1997).
Mohan et al., "Genome Mapping, Molecular Markers and Marker-Assisted Selection Crop Plants", *Mol. Breed.* 3, 87-103 (1997).
Nakane et al., "Nucleotide Sequence of the Shikimate Kinase Gene (*aroI*) of *Bacillus subtilis*", *J. Ferment. Bioeng.* 77, 312-314 (1994).
Nakayashiki et al., "Nucleotide Sequence of a cDNA Clone Encoding Glutamyl-tRNA Reductase from Rice (Accession No. AB011416)", *Plant Physiol.* 117, 332 (1998).
NCBI Accession No. S42508 (May 8, 1993).
NCBI Accession No. D23883 (Nov. 29, 1993).
NCBI Accession No. AAA34069, corresponding to gi:535771 (Sep. 11, 1994).
Norris et al., "Complementation of the Arabidopsis *pds 1* Mutation with the Gene Encoding *p*-Hydroxyphenylpuruvate Dioxygenase", *Plant Physiol.* 117, 1317-1323 (1998).
Oka et al., "Replication Origin of the *Escherichia coli* K-12 Chromosome: The Size and Structure of the Minimum DNA Segment Carrying the Information for Autonomous Replication", *Mol. Gen. Genet.* 178(1), 9-20 (1980).
Okubo et al., "Large Scale cDNA Sequencing for Analysis of Quantitative and Qualitative Aspects of Gene Expression", *Nature Gen.* 2, 173-179 (1992).
Phillips et al., "Isolation and Expression of Three Gibberellin 20-Oxidase cDNA Clones from *Arabidopsis*", *Plant Physiol.* 108(3), 1049-1057 (1995).
Porra, "Recent Progress in Porphyrin and Chlorophyll Biosynthesis", *Photochem. Photobiol.* 65(3), 492-516 (1997).
Russell et al., "Structural Features can be Unconserved in Proteins with Similar Folds. An Analysis of Side-Chain to Side-Chain Contacts Secondary Structure and Accessibility", *J. Mol. Biol.* 244, 332-350 (1994).

Sakamoto et al., "An Overview of Gibberellin Metabolism Enzyme Genes and Their Related Mutants in Rice", *Plant Physiol.* 134, 1642-1653 (2004).

Schmitz et al., "The Tomato *Blind* Gene Encodes a MYB Transcription Factor that Controls the Formation of Lateral Meristems", *Proc. Nat. Acad. Sci.* 99(2), 1064-1069 (2002).

Schünmann et al., "Identification of Three cDNA Clones Expressed in the Leaf Extension Zone and with Altered Patterns of Expression in the *Slender* Mutant of Barley: A Tonoplast Intrinsic Protein, a Putative Structural Protein and Protochlorophylide Oxidoreductase," *Plant Mol. Biol.* 31, 529-537 (1996).

Seffernick et al., "Melamine Deaminase and Atrazine Chlorohydrolase: 98 Percent Identical but Functionally Different", *J. Bacteriol.* 183(8), 2405-2410 (2001).

SIGMA Chemical Catalogue (Sigma Chemical Co.; P.O. Box 14508, St. Louis MO 63178) 1993, product Nos. 01256, 03628, 04375, pp. 736-737.

Smith et al., "Partial Purification and Characterization of the Gibberellin $A_{20}$ 3β-Hydroxylase from Seeds of *Phaseolus vulgaris*", *Plant Physiol.* 94:1390-1401 (1990).

Smith et al., "The First Step of Gibberellin Biosynthesis in Pumpkin is Catalyzed by at Least Two Copalyl Diphosphate Synthases Encoded by Differentially Regulated Genes", *Plant Physiol.* 118, 1411-1419 (1998).

Stammers et al., "Rapid Purification and Characterization of HIV-1 Reverse Transcriptase and RNaseH Engineered to Incorporate a C-terminal Tripeptide α-Tubulin Epitope", *FEBS Lett.* 283(2), 298-302 (1991).

Tanaka et al., "The Third Member of the *hemA* gene Family Encoding Glutamyl-tRNA Reductase in Primarily Expressed in Roots in *Hordeum vulgare*", *Photosynthesis Res.* 53, 161-171 (1997).

Tanksley et al., "Chromosome landing: a paradigm for map-based gene cloning in plants with large genomes", *Trends in Genet.* 11(2), 63-68 (1995).

Tikhonov et al., "Colinearity and its Exceptions in Orthologous *adh* Regions of Maize and Sorghum", *Proc. Natl. Acad. Sci. USA* 96, 7409-7414 (1999).

van de Loo et al., "An Oleate 12-Hydroxylase from *Ricirus communis L.* is a Fatty Acyl Desaturase Homolog", *Proc. Nat. Acad. Sci.* 92, 6743-6747 (1995).

Venter et al., "A New Strategy for Genome Sequencing", *Nature* 381, 364-366 (1996).

Venter et al., "The Sequence of the Human Genome" *Science* 291, 1304-1351 (2001).

Wang et al., "Construction of a Rice Bacterial Artificial Chromosome Library and Identification of Clones Linked to the Xa-21 Disease Resistance Locus", *Plant J.* 7(3), 525-533 (1995).

Wells et al., "The Chemokine Information Source: Identification and Characterization of Novel Chemokines Using the WorldWideWeb and Expressed Sequence Tag Databases", *J. Leukocyte Biol.* 61(5), 545-550 (1997).

Wendel et al., "New Isozyme Systems for Maize (*Zea mays* L.): Aconitate Hydratase, Adenylate Kinase, NADH Dehydrogenase, and Shikimate Dehydrogenase", *Biochem. Genet.* 26(5-6), 421-446 (1988) (Abstract Only).

Wenzel et al., "Physical mapping of the *Mycoplasma pneumoniae* genome", *Nucleic Acids Res.* 16(17), 8323-8336 (1988).

Winkler et al., "The Maize *Dwarf3* Gene Encodes a Cytochrome P450-Mediated Early Step in Gibberellin Biosynthesis", *Plant Cell* 7(8), 1307-1317 (1995).

Woese et al., "Conservation of Primary Structure in 16S Ribosomal RNA", *Nature* 254, 83-85 (1975).

Written Description Training Material, Example 7, pp. 30-32.

Yomo et al., "Histochemical Studies on Protease Formation in the Cotyledons of Germinating Bean Seeds," *Planta* 112(1), 35-43 (1973).

Zhang et al., "Physical Mapping of the Rice Genome with BACs", *Plant Mol. Biol.* 35, 115-127 (1997).

Zhang et al., "Construction and Characterization of Two Rice Bacterial Artificial Chromosome Libraries from the Parents of a Permanent Recombinant Inbred Mapping Population", *Mol. Breeding* 2, 11-24 (1996).

Zwick et al., "Physical Mapping of the *liguleless* Linkage Group in *Sorghum bicolor* Using Rice RFLP-Selected Sorghum BACs", *Genetics* 248, 1983-1992 (1998).

U.S. Appl. No. 09/815,254, filed Mar. 23, 2001, Boukharov et al.
U.S. Appl. No. 10/425,114, filed Mar. 28, 2003, Liu et al.
U.S. Appl. No. 11/329,175, filed Jan. 11, 2006, CaJacob et al.
U.S. Appl. No. 11/329,160, filed Jan. 11, 2006, Bhat et al.
U.S. Appl. No. 11/329,388, filed Jan. 11, 2006, Andersen et al.
U.S. Appl. No. 11/330,082, filed Jan. 12, 2006, Buehler et al.
U.S. Appl. No. 11/330,083, filed Jan. 12, 2006, Byrum et al.
U.S. Appl. No. 11/331,019, filed Jan. 13, 2006, Fincher et al.
U.S. Appl. No. 11/331,032, filed Jan. 13, 2006, Fincher et al.
U.S. Appl. No. 11/352,295, filed Feb. 13, 2006, Andersen et al.
U.S. Appl. No. 11/353,150, filed Feb. 14, 2006, Andersen et al.
U.S. Appl. No. 11/486,299, filed Jul. 14, 2006, Byrum.
U.S. Appl. No. 11/490,207, filed Jul. 21, 2006, Brown et al.
U.S. Appl. No. 11/491,125, filed Jul. 24, 2006, Boukharov et al.
U.S. Appl. No. 11/491,178, filed Jul. 24, 2006, Hinkle et al.
U.S. Appl. No. 11/491,371, filed Jul. 24, 2006, Byrum.
U.S. Appl. No. 11/497,489, filed Aug. 2, 2006, Byrum et al.
U.S. Appl. No. 11/503,243, filed Aug. 14, 2006, Kovalic et al.
U.S. Appl. No. 11/520,715, filed Sep. 14, 2006, Liu et al.
U.S. Appl. No. 11/521,349, filed Sep. 15, 2006, Byrum et al.
U.S. Appl. No. 11/595,983, filed Nov. 13, 2006, Boukharov et al.

BLASTN Search of "Nucleotide collection (nr/nt)" database performed Dec. 16, 2008 (11 pages).

BLASTX Search of "Non-redundant protein sequences (nr)" database performed Dec. 16, 2008, (35 pages).

BLASTP Search of "Swissprot" database performed Dec. 16, 2008, (26 pages).

NCBI Record by BLASTX search conducted December; Accession AAC39327 [gi:2801448] obtained Dec. 19, 2008.

NCBI Record by BLASTX search conducted December; Accession ACF80972 [gi:194693776] obtained Dec. 19, 2008.

NCBI Record by BLASTX search conducted December; Accession AAF69157 [gi:7767660] obtained Dec. 19, 2008.

NCBI Record by BLASTX search conducted December; Accession EEC75939 [gi:218193512] obtained Dec. 19, 2008.

NCBI Record by BLASTX search conducted December; Accession ABK93246 [gi:118482654] obtained Dec. 19, 2008.

NCBI Record by BLASTX search conducted December; Accession XP_646882 [gi:66827055] obtained Dec. 19, 2008.

NCBI Record by BLASTX search conducted December; Accession XP_001624113 [gi:156357206] obtained Dec. 19, 2008.

NCBI Record by BLASTX search conducted December; Accession XP_974790 [gi:91079008] obtained Dec. 19, 2008.

NCBI Record by BLASTX search conducted December; Accession Q4VBH4 [gi:93140723] obtained Dec. 19, 2008.

NCBI Record by BLASTX search conducted December; Accession AAH95816 [gi:66267363] obtained Dec. 19, 2008.

NCBI Record by BLASTX search conducted December; Accession EEA47037 [gi:210098935] obtained Dec. 19, 2008.

NCBI Record by BLASTX search conducted December; Accession XP_001662805 [gi:157133217] obtained Dec. 19, 2008.

NCBI Record by BLASTX search conducted December; Accession BAA91954 [gi:7023411] obtained Dec. 19, 2008.

NCBI Record by BLASTX search conducted December; Accession XP_001927700 [gi:194036624] obtained Dec. 19, 2008.

NCBI Record by BLASTX search conducted December; Accession XP_001491727 [gi:149721310] obtained Dec. 19, 2008.

NCBI Record by BLASTX search conducted December; Accession EDL14346 [gi:148682399] obtained Dec. 19, 2008.

NCBI Record by BLASTX search conducted December; Accession EAW87009 [gi:119607415] obtained Dec. 19, 2008.

NCBI Record by BLASTX search conducted December; Accession XP_001062727 [gi:109475992] obtained Dec. 19, 2008.

NCBI Record by BLASTX search conducted December; Accession XP_001085749 [gi:109086705] obtained Dec. 19, 2008.

NCBI Record by BLASTX search conducted December; Accession NP_080049 [gi:110625675] obtained Dec. 19, 2008.

NCBI Record by BLASTX search conducted December; Accession BAB13883 [gi:10432979] obtained Dec. 19, 2008.

NCBI Record by BLASTX search conducted December; Accession NP_060769 [gi:145301543] obtained Dec. 19, 2008.
NCBI Record by BLASTX search conducted December; Accession NP_001001481 [gi:47933381] obtained Dec. 19, 2008.
NCBI Record by BLASTX search conducted December; Accession XP_001378231 [gi:126321270] obtained Dec. 19, 2008.
NCBI Record by BLASTX search conducted December; Accession XP_418298 [gi:50731626] obtained Dec. 19, 2008.
NCBI Record by BLASTX search conducted December; Accession NP_001016132 [gi:62859305] obtained Dec. 19, 2008.
NCBI Record by BLASTX search conducted December; Accession AAI16564 [gi:95132432] obtained Dec. 19, 2008.
NCBI Record by BLASTX search conducted December; Accession NP_001038758 [gi:147900051] obtained Dec. 19, 2008.
NCBI Record by BLASTX search conducted December; Accession EAZ28149 [gi:125587485] obtained Dec. 19, 2008.
NCBI Record by BLASTX search conducted December; Accession EEC09834 [gi:215500340] obtained Dec. 19, 2008.
NCBI Record by BLASTX search conducted December; Accession XP_001688635 [gi:158293993] obtained Dec. 19, 2008.
NCBI Record by BLASTX search conducted December; Accession XP_315339 [gi:158293991] obtained Dec. 19, 2008.
NCBI Record by BLASTX search conducted December; Accession XP_001659332 [gi:157119091] obtained Dec. 19, 2008.
NCBI Record by BLASTX search conducted December; Accession NP_493587 [gi:17510293] obtained Dec. 19, 2008.
NCBI Record by BLASTX search conducted December; Accession AAQ97779 [gi:37681803] obtained Dec. 19, 2008.
NCBI Record by BLASTX search conducted December; Accession XP_392626 [gi:66549055] obtained Dec. 19, 2008.
NCBI Record by BLASTX search conducted December; Accession XP_001901039 [gi:170592573] obtained Dec. 19, 2008.
NCBI Record by BLASTX search conducted December; Accession BAB29807 [gi:12853653] obtained Dec. 19, 2008.
NCBI Record by BLASTX search conducted December; Accession BAC37094 [gi:26346891] obtained Dec. 19, 2008.
NCBI Record by BLASTX search conducted December; Accession EAW87010 [gi:119607416] obtained Dec. 19, 2008.
NCBI Record by BLASTX search conducted December; Accession CAF98020 [gi:47223533] obtained Dec. 19, 2008.
NCBI Record by BLASTX search conducted December; Accession XP_001950447 [gi:193609423] obtained Dec. 19, 2008.
NCBI Record by BLASTX search conducted December; Accession XP_787137 [gi:115663109] obtained Dec. 19, 2008.
NCBI Record by BLASTP search conducted December; Accession Q9FMM0 [gi:75334076] obtained Dec. 19, 2008.
NCBI Record by BLASTP search conducted December; Accession P42743 [gi:26454674] obtained Dec. 19, 2008.
NCBI Record by BLASTP search conducted December; Accession Q9FWT2 [gi:75334430] obtained Dec. 19, 2008.
NCBI Record by BLASTP search conducted December; Accession O23239 [gi:75318090] obtained Dec. 19, 2008.
NCBI Record by BLASTP search conducted December; Accession Q55EY8 [gi:74897457] obtained Dec. 19, 2008.
NCBI Record by BLASTP search conducted December; Accession Q4VBH4 [gi:93140723] obtained Dec. 19, 2008.
NCBI Record by BLASTP search conducted December; Accession Q96B02 [gi:74751754] obtained Dec. 19, 2008.
NCBI Record by BLASTP search conducted December; Accession Q8VDW4 [gi:81901996] obtained Dec. 19, 2008.
NCBI Record by BLASTP search conducted December; Accession P51668 [gi:1717848] obtained Dec. 19, 2008.
NCBI Record by BLASTN search conducted December; Accession 195620115 [gi:195620115] obtained Dec. 19, 2008.
NCBI Record by BLASTN search conducted December; Accession 194693775 [gi:194693775] obtained Dec. 19, 2008.
NCBI Record by BLASTN search conducted December; Accession 21207415 [gi:21207415] obtained Dec. 19, 2008.
NCBI Record by BLASTN search conducted December; Accession 195650616 [gi:195650616] obtained Dec. 19, 2008.
NCBI Record by BLASTN search conducted December; Accession 195623547 [gi:195623547] obtained Dec. 19, 2008.
NCBI Record by BLASTN search conducted December; Accession 195610241 [gi:195610241] obtained Dec. 19, 2008.
NCBI Record by BLASTN search conducted December; Accession 115454610 [gi:115454610] obtained Dec. 19, 2008.
NCBI Record by BLASTN search conducted December; Accession 32989018 [gi:32989018] obtained Dec. 19, 2008.
NCBI Record by BLASTN search conducted December; Accession 195604635 [gi:195604635] obtained Dec. 19, 2008.
NCBI Record by BLASTN search conducted December; Accession 212722863 [gi:212722863] obtained Dec. 19, 2008.
NCBI Record by BLASTN search conducted December; Accession 54652986 [gi:54652986] obtained Dec. 19, 2008.
NCBI Record by BLASTN search conducted December; Accession 157888166 [gi:157888166] obtained Dec. 19, 2008.
NCBI Record by BLASTN search conducted December; Accession 57164485 [gi:57164485] obtained Dec. 19, 2008.
NCBI Record by BLASTN search conducted December; Accession 31712067 [gi:31712067] obtained Dec. 19, 2008.
NCBI Record by BLASTN search conducted December; Accession 58530789 [gi:58530789] obtained Dec. 19, 2008.
NCBI Record by BLASTX search conducted December; Accession ACG31888 [gi:195620116] obtained Dec. 19, 2008.
NCBI Record by BLASTX search conducted December; Accession NP_001050906 [gi:115454611] obtained Dec. 19, 2008.
NCBI Record by BLASTX search conducted December; Accession ACG24564 [gi:195605468] obtained Dec. 19, 2008.
NCBI Record by BLASTX search conducted December; Accession ACF83463 [gi:194698758] obtained Dec. 19, 2008.
NCBI Record by BLASTX search conducted December; Accession ACG36729 [gi:195633091] obtained Dec. 19, 2008.
NCBI Record by BLASTX search conducted December; Accession NP_001067367 [gi:115489760] obtained Dec. 19, 2008.
NCBI Record by BLASTX search conducted December; Accession NP_568619 [gi:18422281] obtained Dec. 19, 2008.
NCBI Record by BLASTX search conducted December; Accession ABK95735 [gi:118487824] obtained Dec. 19, 2008.
NCBI Record by BLASTX search conducted December; Accession CAO48290 [gi:157354944] obtained Dec. 19, 2008.
NCBI Record by BLASTX search conducted December; Accession ABR14728 [gi:148841111] obtained Dec. 19, 2008.
NCBI Record by BLASTX search conducted December; Accession ABK21203 [gi:116779255] obtained Dec. 19, 2008.
NCBI Record by BLASTX search conducted December; Accession CAA48378 [gi:22658] obtained Dec. 19, 2008.
NCBI Record by BLASTX search conducted December; Accession NP_564493 [gi:18401461] obtained Dec. 19, 2008.
NCBI Record by BLASTX search conducted December; Accession NP_565110 [gi:18410856] obtained Dec. 19, 2008.
NCBI Record by BLASTX search conducted December; Accession CAN82081 [gi:147844523] obtained Dec. 19, 2008.
NCBI Record by BLASTX search conducted December; Accession ACG33604 [gi:195623548] obtained Dec. 19, 2008.
NCBI Record by BLASTX search conducted December; Accession ABK93923 [gi:118484075] obtained Dec. 19, 2008.
NCBI Record by BLASTX search conducted December; Accession CAA10494 [gi:4090259] obtained Dec. 19, 2008.
NCBI Record by BLASTX search conducted December; Accession ABK23710 [gi:116785406] obtained Dec. 19, 2008.
NCBI Record by BLASTX search conducted December; Accession XP_001776786 [gi:168048665] obtained Dec. 19, 2008.
NCBI Record by BLASTX search conducted December; Accession EAZ21342 [gi:125580196] obtained Dec. 19, 2008.
NCBI Record by BLASTX search conducted December; Accession NP_568004 [gi:18419831] obtained Dec. 19, 2008.
NCBI Record by BLASTX search conducted December; Accession AAC39325 [gi:2801444] obtained Dec. 19, 2008.
NCBI Record by BLASTX search conducted December; Accession ABG22107 [gi:108863022] obtained Dec. 19, 2008.
NCBI Record by BLASTX search conducted December; Accession XP_001775540 [gi:168046155] obtained Dec. 19, 2008.
NCBI Record by BLASTX search conducted December; Accession AAP68373 [gi:31712068] obtained Dec. 19, 2008.

* cited by examiner

NUCLEIC ACID MOLECULES SEQ ID NO. 16372 AND OTHER MOLECULES ASSOCIATED WITH PLANTS

CROSS REFERENCE TO RELATED APPLICATIONS

This application is a continuation under 35 U.S.C. § 120 of U.S. application Ser. No. 09/696,664 filed Oct. 25, 2000 now abandoned, which is a continuation-in-part of U.S. application Ser. No. 09/553,094, filed Apr. 18, 2000 now abandoned, which is a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Jun. 9, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/553,094 is also a continuation-in-part of U.S. application Ser. No. 09/394,745, filed Sep. 15, 1999, which is a continuation-in-part of U.S. application Ser. No. 09/237,183, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln.

Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, flied Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Jun. 6, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/394,745 also claims the benefit of U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,707, filed Sep. 25, 1998; and to U.S. Provisional Appln. Ser. No. 60/104,119, filed Oct. 13, 1998; and to U.S. Provisional Appln. Ser. No. 60/104,121, filed Oct. 13, 1998; and to U.S. Provisional Appln. Ser. No. 60/104,123, filed Oct. 13, 1998; and to U.S. Provisional Appln. Ser. No. 60/104,124, filed Oct. 13, 1998; and to U.S. Provisional Appln. Ser. No. 60/104,127, filed Oct. 13, 1998; and to U.S. Provisional Appln. Ser. No. 60/111,033, filed Dec. 4, 1998; and to U.S. Provisional Appln. Ser. No. 60/130,180, filed Apr. 20, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999; and to U.S. Provisional Appln. Ser. No. 60/146,904, filed Aug. 2, 1999; and to U.S. Provisional Appln. Ser. No. 60/146,907, filed Aug. 2, 1999. U.S. appication Ser. No. 09/553,094 also claims the benefit of U.S. Provisional Appln. Ser. No. 60/130,178, filed Apr. 20, 1999; and to U.S. Provisional Appln. Ser. No. 60/130,180, filed Apr. 20, 1999; and to U.S. Provisional Appln. Ser. No. 60/132,860, filed May 7, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999; and to U.S. Provisional Appln. Ser. No. 60/146,904, filed Aug. 2, 1999; and to U.S. Provisional Appln. Ser. No. 60/146,907, filed Aug. 2, 1999; and to U.S. Provisional Appln. Ser. No. 60/161,619, filed Oct. 26, 1999. U.S. application Ser. No. 09/696,664 is also a continuation-in-part of U.S. application Ser. No. 09/371,146, filed Aug. 9, 1999 now abandoned, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/371,146 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/371,146 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/371,146 is also a continuation-in-part of U.S. application Ser. No. 09/244,000, filed Feb. 8, 1999 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun.

18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/244,000 also claims the benefit of U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/086,183, filed May 21, 1998; and to U.S. Provisional Appln. Ser. No. 60/086,188, filed May 21, 1998. U.S. application Ser. No. 09/371,146 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/371,146 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/371,146 is also a continuation-in-part of U.S. application Ser. No. 09/304,517, filed May 6, 1999 (abandoned). U.S. application Ser. No. 09/371,146 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998;

and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S.

Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/267,199, filed Mar. 12, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Proyisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, flIed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 also claims the benefit of U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S.

Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/300,482, filed Apr. 28, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/300,482 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/300,482 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/300,482 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/300,482 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/300,482 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S.

application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998;

and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 is also a continuation-in-part of U.S. application Ser. No. 09/267,199, filed Mar. 12, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S.

application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. Appln. Ser. No. 09/233,218, filed Jan. 20, 1999, which is a continuation-in-part of U.S. Appln. Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S.

Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, flied Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. 14o. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 also claims the benefit of U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 also claims the benefit of U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/333,535, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 is also a continuation-in-part of U.S. application Ser. No. 09/206,040, filed Dec. 4, 1998 (abandoned), which claims the benefit of U.S. Provisional Appln. Ser. No. 60/100,647, filed Sep. 16, 1998. U.S. application Ser. No. 09/333,535 is also a continuation-in-part of U.S. application Ser. No. 09/210,297, filed Dec. 8, 1998 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 is also a continuation-in-part of U.S. application Ser. No. 09/244,000, filed Feb. 8, 1999 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/244,000 also claims the benefit of U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/086,183, filed May 21, 1998; and to U.S. Provisional Appln. Ser. No. 60/086,188, filed May 21, 1998. U.S. application Ser. No. 09/333,535 is also a continuation-in-part of U.S. application Ser. No. 09/263,191, filed Mar. 5, 1999 (abandoned). U.S. application Ser. No. 09/333,535 is also a continuation-in-part of U.S. application Ser. No. 09/283,466, filed Apr. 2, 1999 (abandoned). U.S. application Ser. No. 09/333,535 is also a continuation-in-part of U.S. application Ser. No. 09/306,349, filed May 10, 1999 (abandoned). U.S.

application Ser. No. 09/333,535 is also a continuation-in-part of U.S. application Ser. No. 09/199,129, filed Nov. 24, 1998, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. Appln. Ser. No, 09/199,129 also claims the benefit of U.S. Provisional Appln. Ser. No. 60/067,000, filed Nov. 24, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/089,524, filed Jun. 16, 1998; and to U.S. Provisional Appln. Ser. No. 60/089,793, filed Jun. 18, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 also claims the benefit of U.S. Provisional Appln. Ser. No. 60/089, 524, filed Jun. 16, 1998; and to U.S. Provisional Appln. Ser. No. 60/089,793, filed Jun. 18, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, and to U.S. Provisional Appln. Ser. No. 60/108,996, filed Nov. 18, 1998; and to U.S. Provisional Appln. Ser. No. 60/109,018, filed Nov. 18, 1998; and to U.S. Provisional Appln. Ser. No. 60/111,981, filed Dec. 11, 1998; and to U.S. Provisional Appln. Ser. No. 60/112,221, filed Dec. 14, 1998; and to U.S. Provisional Appln. Ser. No. 60/112,229, filed Dec. 14, 1998; and to U.S. Provisional Appln. Ser. No. 60/112,808, filed Dec. 18, 1998; and to U.S. Provisional Appln. Ser. No. 60/113,224, filed Dec. 22, 1998; and to U.S. Provisional Appln. Ser. No. 60/125,816, filed Mar. 23, 1999; and to U.S. Provisional Appln. Ser. No. 60/125,817, filed Mar. 23, 1999; and to U.S. Provisional Appln. Ser. No. 60/125,818, filed Mar. 23, 1999; and to U.S. Provisional Appln. Ser. No. 60/130,174, filed Apr. 20, 1999; and to U.S. Provisional Appln. Ser. No. 60/130,464, filed Apr. 22, 1999; and to U.S. Provisional Appln. Ser. No. 60/133,690, filed May 10, 1999; and to U.S. Provisional Appln. Ser. No. 60/133,691, filed May 10, 1999; and to U.S. Provisional Appln. Ser. No. 60/133,692, filed May 10, 1999. U.S. application Ser. No. 09/371,146 also claims the benefit of U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/100,672, filed Sep. 16, 1998; and to U.S. Provisional Appln. Ser. No. 60/100,963, filed Sep. 17, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/101,708, filed Sep. 25, 1998; and to U.S. Provisional Appln. Ser. No. 60/101,709, filed Sep. 25, 1998; and to U.S. Provisional Appln. Ser. No. 60/104,119, filed Oct. 13, 1998; and to U.S. Provisional Appln. Ser. No. 60/104,121, filed Oct. 13, 1998; and to U.S. Provisional Appln. Ser. No. 60/104,122, filed Oct. 13, 1998; and to U.S. Provisional Appln. Ser. No. 60/104,123, filed Oct. 13, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/108,996, filed Nov. 18, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998; and to U.S. Provisional Appln. Ser. No. 60/112,221, filed Dec. 14, 1998; and to U.S. Provisional Appln. Ser. No. 60/112,229, filed Dec. 14, 1998; and to U.S. Provisional Appln. Ser. No. 60/112,807, filed Dec. 18, 1998; and to U.S. Provisional Appln. Ser. No. 60/113,224, filed Dec. 22, 1998; and to U.S. Provisional Appln. Ser. No. 60/130,174, filed Apr. 20, 1999; and to U.S. Provisional Appln. Ser. No. 60/130,177, filed Apr. 20, 1999; and to U.S. Provisional Appln. Ser. No. 60/130,178, filed Apr. 20, 1999; and to U.S. Provisional Appln. Ser. No. 60/130,179, filed Apr. 20, 1999; and to U.S. Provisional Appln. Ser. No. 60/130,180, filed Apr. 20, 1999; and to U.S. Provisional Appln. Ser. No. 60/130,181, filed Apr. 20, 1999; and to U.S. Provisional Appln. Ser. No. 60/132,860, filed May 7, 1999; and to U.S. Provisional Appln. Ser. No. 60/133,691, filed May 10, 1999; and to U.S. Provisional Appln. Ser. No. 60/133,692, filed May 10, 1999; and to U.S. Provisional Appln. Ser. No. 60/141,128, filed Jun. 28, 1999; and to U.S. Provisional Appln. Ser. No. 60/141,134, filed Jun. 28, 1999; and to U.S. Provisional Appln. Ser. No. 60/144,084, filed Jul. 16, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999. U.S. application Ser. No. 09/696,664 is also a continuation-in-part of U.S. application Ser. No. 09/565,306, filed May 4, 2002, which is a continuation-in-part of U.S. application Ser. No. 09/371,146, filed Aug. 9, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/371,146 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/371,146 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/371,146 is also a continuation-in-part of U.S. application Ser. No. 09/244,000, filed Feb. 8, 1999 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998;

and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/244,000 also claims the benefit of U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/086,183, filed May 21, 1998; and to U.S. Provisional Appln. Ser. No. 60/086,188, filed May 21, 1998. U.S. application Ser. No. 09/371,146 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/371,146 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/371,146 is also a continuation-in-part of U.S. application Ser. No. 09/304,517, filed May 6, 1999 (abandoned). U.S. application Ser. No. 09/371,146 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No.

60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998;

and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/267,199, filed Mar. 12, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, flIed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998;

and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. Appln. Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/300,482, filed Apr. 28, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/300,482 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/300,482 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/300,482 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/300,482 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/300,482 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S.

Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, flIed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 is also a continuation-in-part of U.S. application Ser. No. 09/267,199, filed Mar. 12, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln.

Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No.

60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 also claims the benefit of U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 also claims the benefit of U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No.

60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/333,535, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, fIled Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 is also a continuation-in-part of U.S. application Ser. No. 09/206,040, filed Dec. 4, 1998 (abandoned), which claims the benefit of U.S. Provisional Appln. Ser. No. 60/100,647, filed Sep. 16, 1998. U.S. application Ser. No. 09/333,535 is also a continuation-in-part of U.S. application Ser. No. 09/210,297, filed Dec. 8, 1998 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 is also a continuation-in-part of U.S. application Ser. No. 09/244,000, filed Feb. 8, 1999 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/244,000 also claims the benefit of U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/086,183, filed May 21, 1998; and to U.S. Provisional Appln. Ser. No. 60/086,188, filed May 21, 1998. U.S. application Ser. No. 09/333,535 is also a continuation-in-part of U.S. application Ser. No. 09/263,191, filed Mar. 5, 1999 (abandoned). U.S. application Ser. No. 09/333,535 is also a continuation-in-part of U.S. application Ser. No. 09/283,466, filed Apr. 2, 1999 (abandoned). U.S. application Ser. No. 09/333,535 is also a continuation-in-part of U.S. application Ser. No. 09/306,349, filed May 10, 1999 (abandoned). U.S. application Ser. No. 09/333,535 is also a continuation-in-part of U.S. application Ser. No. 09/199,129, filed Nov. 24, 1998, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S.

Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. Appln. Ser. No, 09/199,129 also claims the benefit of U.S. Provisional Appln. Ser. No. 60/067,000, filed Nov. 24, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/089,524, filed Jun. 16, 1998; and to U.S. Provisional Appln. Ser. No. 60/089,793, filed Jun. 18, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 also claims the benefit of U.S. Provisional Appln. Ser. No. 60/089,524, filed Jun. 16, 1998; and to U.S. Provisional Appln. Ser. No. 60/089,793, filed Jun. 18, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, and to U.S. Provisional Appln. Ser. No. 60/108,996, filed Nov. 18, 1998; and to U.S. Provisional Appln. Ser. No. 60/109,018, filed Nov. 18, 1998; and to U.S. Provisional Appln. Ser. No. 60/111,981, filed Dec. 11, 1998; and to U.S. Provisional Appln. Ser. No. 60/112,221, filed Dec. 14, 1998; and to U.S. Provisional Appln. Ser. No. 60/112,229, filed Dec. 14, 1998; and to U.S. Provisional Appln. Ser. No. 60/112,808, filed Dec. 18, 1998; and to U.S. Provisional Appln. Ser. No. 60/113,224, filed Dec. 22, 1998; and to U.S. Provisional Appln. Ser. No. 60/125,816, filed Mar. 23, 1999; and to U.S. Provisional Appln. Ser. No. 60/125,817, filed Mar. 23, 1999; and to U.S. Provisional Appln. Ser. No. 60/125,818, filed Mar. 23, 1999; and to U.S. Provisional Appln. Ser. No. 60/130,174, filed Apr. 20, 1999; and to U.S. Provisional Appln. Ser. No. 60/130,464, filed Apr. 22, 1999; and to U.S. Provisional Appln. Ser. No. 60/133,690, filed May 10, 1999; and to U.S. Provisional Appln. Ser. No. 60/133,691, filed May 10, 1999; and to U.S. Provisional Appln. Ser. No. 60/133,692, filed May 10, 1999. U.S. application Ser. No. 09/371,146 also claims the benefit of U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/100,672, filed Sep. 16, 1998; and to U.S. Provisional Appln. Ser. No. 60/100,963, filed Sep. 17, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/101,708, filed Sep. 25, 1998; and to U.S. Provisional Appln. Ser. No. 60/101,709, filed Sep. 25, 1998; and to U.S. Provisional Appln. Ser. No. 60/104,119, filed Oct. 13, 1998; and to U.S. Provisional Appln. Ser. No. 60/104,121, filed Oct. 13, 1998; and to U.S. Provisional Appln. Ser. No. 60/104,122, filed Oct. 13, 1998; and to U.S. Provisional Appln. Ser. No. 60/104,123, filed Oct. 13, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/108,996, filed Nov. 18, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998; and to U.S. Provisional Appln. Ser. No. 60/112,221, filed Dec. 14, 1998; and to U.S. Provisional Appln. Ser. No. 60/112,229, filed Dec. 14, 1998; and to U.S. Provisional Appln. Ser. No. 60/112,807, filed Dec. 18, 1998; and to U.S. Provisional Appln. Ser. No. 60/113,224, filed Dec. 22, 1998; and to U.S. Provisional Appln. Ser. No. 60/130,174, filed Apr. 20, 1999; and to U.S. Provisional Appln. Ser. No. 60/130,177, filed Apr. 20, 1999; and to U.S. Provisional Appln. Ser. No. 60/130,178, filed Apr. 20, 1999; and to U.S. Provisional Appln. Ser. No. 60/130,179, filed Apr. 20, 1999; and to U.S. Provisional Appln. Ser. No. 60/130,180, filed Apr. 20, 1999; and to U.S. Provisional Appln. Ser. No. 60/130,181, filed Apr. 20, 1999; and to U.S. Provisional Appln. Ser. No. 60/132,860, filed May 7, 1999; and to U.S. Provisional Appln. Ser. No. 60/133,691, filed May 10, 1999; and to U.S. Provisional Appln. Ser. No. 60/133,692, filed May 10, 1999; and to U.S. Provisional Appln. Ser. No. 60/141,128, filed Jun. 28, 1999; and to U.S. Provisional Appln. Ser. No. 60/141,134, filed Jun. 28, 1999; and to U.S. Provisional Appln. Ser. No. 60/144,084, filed Jul. 16, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999. U.S. application Ser. No. 09/565,306 is also a continuation-in-part of U.S. application Ser. No. 09/394,745, filed Sep. 15, 1999, which is a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/394,745 also claims the benefit of U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,707, filed Sep. 25, 1998; and to U.S. Provisional Appln. Ser. No. 60/104,119, filed Oct. 13, 1998; and to U.S. Provisional Appln. Ser. No. 60/104,121, filed Oct. 13, 1998; and to U.S. Provisional Appln. Ser. No. 60/104,123, filed Oct. 13, 1998; and to U.S. Provisional Appln. Ser. No. 60/104,124, filed Oct. 13, 1998; and to U.S. Provisional Appln. Ser. No. 60/104,127, filed Oct. 13, 1998; and to U.S. Provisional Appln. Ser. No. 60/111,033, filed Dec. 4, 1998; and to U.S. Provisional Appln. Ser. No. 60/130,180, filed Apr. 20, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999; and to U.S. Provisional Appln. Ser. No. 60/146,904, filed Aug. 2, 1999; and to U.S. Provisional Appln. Ser. No. 60/146,907, filed Aug. 2, 1999. U.S. application Ser. No. 09/565,306 is also a continuation-in-part of U.S. application Ser. No. 09/553,094, filed Apr. 18, 2000, which is a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998;

and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/553,094 is also a continuation-in-part of U.S. application Ser. No. 09/371,146, filed Aug. 9, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/371,146 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/371,146 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/371,146 is also a continuation-in-part of U.S. application Ser. No. 09/244,000, filed Feb. 8, 1999 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/244,000 also claims the benefit of U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/086,183, filed May 21, 1998; and to U.S. Provisional Appln. Ser. No. 60/086,188, filed May 21, 1998. U.S. application Ser. No. 09/371,146 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/371,146 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/371,146 is also a continuation-in-part of U.S. application Ser. No. 09/304,517, filed May 6, 1999 (abandoned). U.S. application Ser. No. 09/371,146 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln.

Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, flied May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, flied May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/267,199, filed Mar. 12, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S.

Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998;

and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S.

Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 also claims the benefit of U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/300,482, filed Apr. 28, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/300,482 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/300,482 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/300,482 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/300,482 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/300,482 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998;

and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 is also a continuation-in-part of U.S. application Ser. No. 09/267,199, filed Mar. 12, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No.

60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional .Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No.

60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S.

Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998;

and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 also claims the benefit of U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/300,482 also claims the benefit of U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/371,146 is also a continuation-in-part of U.S. application Ser. No. 09/333,535, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No.

60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 is also a continuation-in-part of U.S. application Ser. No. 09/206,040, filed Dec. 4, 1998 (abandoned), which claims the benefit of U.S. Provisional Appln. Ser. No. 60/100,647, filed Sep. 16, 1998. U.S. application Ser. No. 09/333,535 is also a continuation-in-part of U.S. application Ser. No. 09/210,297, filed Dec. 8, 1998 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 is also a continuation-in-part of U.S. application Ser. No. 09/244,000, filed Feb. 8, 1999 (abandoned), which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/244,000 also claims the benefit of U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/086,183, filed May 21, 1998; and to U.S. Provisional Appln. Ser. No. 60/086,188, filed May 21, 1998. U.S. application Ser. No. 09/333,535 is also a continuation-in-part of U.S. application Ser. No. 09/263,191, filed Mar. 5, 1999 (abandoned). U.S. application Ser. No. 09/333,535 is also a continuation-in-part of U.S. application Ser. No. 09/283,466, filed Apr. 2, 1999 (abandoned). U.S. application Ser. No. 09/333,535 is also a continuation-in-part of U.S. application Ser. No. 09/306,349, filed May 10, 1999 (abandoned). U.S. application Ser. No. 09/333,535 is also a continuation-in-part of U.S. application Ser. No. 09/199,129, filed Nov. 24, 1998, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. Appln. Ser. No, 09/199,129 also claims the benefit of U.S. Provisional Appln. Ser. No. 60/067,000, filed Nov. 24, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/089,524, filed Jun. 16, 1998; and to U.S. Provisional Appln. Ser. No. 60/089,793, filed Jun. 18, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/333,535 also claims the benefit of U.S. Provisional Appln. Ser. No. 60/089,524, filed Jun. 16, 1998; and to U.S. Provisional Appln. Ser. No. 60/089,793, filed Jun. 18, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998; and to U.S. Provisional Appln. Ser. No. 60/111,981, filed Dec. 11, 1998; and to U.S. Provisional Appln. Ser. No. 60/112,221, filed Dec. 14, 1998; and to U.S. Provisional Appln. Ser. No. 60/112,229, filed Dec. 14, 1998; and to U.S. Provisional Appln. Ser. No. 60/112,808, filed Dec. 18, 1998; and to U.S. Provisional Appln. Ser. No. 60/113,224, filed Dec. 22, 1998; and to U.S. Provisional Appln. Ser. No. 60/125,816, filed Mar. 23, 1999; and to U.S. Provisional Appln. Ser. No. 60/125,817, filed Mar. 23, 1999; and to U.S. Provisional Appln. Ser. No. 60/125,818, filed Mar. 23, 1999; and to U.S. Provisional Appln. Ser. No. 60/130,174, filed Apr. 20, 1999; and to U.S. Provisional Appln. Ser. No. 60/130,464, filed Apr. 22, 1999; and to U.S. Provisional Appln. Ser. No. 60/133,690, filed May 10, 1999; and to U.S. Provisional Appln. Ser. No. 60/133,691, filed May 10, 1999; and to U.S. Provisional Appln. Ser. No. 60/133,692, filed May 10, 1999. U.S. application Ser. No. 09/371,146 also claims the benefit of U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/100,672, filed Sep. 16, 1998; and to U.S. Provisional Appln. Ser. No. 60/100,963, filed Sep. 17, 1998; and to U.S. Provisional Appln. Ser. No. 60/101,130, filed Sep. 21, 1998; and to U.S. Provisional Appln. Ser. No. 60/101,131, filed Sep. 21, 1998; and to U.S. Provisional Appln. Ser. No. 60/101,132, filed Sep. 21, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/101,708, filed Sep. 25, 1998; and to U.S. Provisional Appln. Ser. No. 60/101,709, filed Sep. 25, 1998; and to U.S. Provisional Appln. Ser. No. 60/104,119, filed Oct. 13, 1998; and to U.S. Provisional Appln. Ser. No. 60/104,121, filed Oct. 13, 1998; and to U.S. Provisional Appln. Ser. No. 60/104,122, filed Oct. 13, 1998; and to U.S. Provisional Appln. Ser. No. 60/104,123, filed Oct. 13, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/108,996, filed Nov. 18, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998; and to U.S. Provisional Appln. Ser. No. 60/112,221, filed Dec. 14, 1998; and to U.S. Provisional Appln. Ser. No. 60/112,229, filed Dec. 14, 1998; and to U.S. Provisional Appln. Ser. No. 60/112,807, filed Dec. 18, 1998; and to U.S. Provisional Appln. Ser. No. 60/113,224, filed Dec. 22, 1998; and to U.S. Provisional Appln. Ser. No. 60/130,174, filed Apr. 20, 1999; and to U.S. Provisional Appln. Ser. No. 60/130,177, filed Apr. 20, 1999; and to U.S. Provisional Appln. Ser. No. 60/130,178, filed Apr. 20, 1999; and to U.S. Provisional Appln. Ser. No. 60/130,179, filed Apr. 20, 1999; and to U.S. Provisional Appln. Ser. No. 60/130,180, filed Apr.

20, 1999; and to U.S. Provisional Appln. Ser. No. 60/130,181, filed Apr. 20, 1999; and to U.S. Provisional Appln. Ser. No. 60/132,860, filed May 7, 1999; and to U.S. Provisional Appln. Ser. No. 60/133,691, filed May 10, 1999; and to U.S. Provisional Appln. Ser. No. 60/133,692, filed May 10, 1999; and to U.S. Provisional Appln. Ser. No. 60/141,128, filed Jun. 28, 1999; and to U.S. Provisional Appln. Ser. No. 60/141,134, filed Jun. 28, 1999; and to U.S. Provisional Appln. Ser. No. 60/144,084, filed Jul. 16, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999. U.S. application Ser. No. 09/553,094 is also a continuation-in-part of U.S. application Ser. No. 09/394,745, filed Sep. 15, 1999, which is a continuation-in-part of U.S. application Ser. No. 09/237,183, filed Jan. 26, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional application Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No.

60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/394,745 also claims the benefit of U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,707, filed Sep. 25, 1998; and to U.S. Provisional Appln. Ser. No. 60/104,119, filed Oct. 13, 1998; and to U.S. Provisional Appln. Ser. No. 60/104,121, filed Oct. 13, 1998; and to U.S. Provisional Appln. Ser. No. 60/104,123, filed Oct. 13, 1998; and to U.S. Provisional Appln. Ser. No. 60/104,124, filed Oct. 13, 1998; and to U.S. Provisional Appln. Ser. No. 60/104,127, filed Oct. 13, 1998; and to U.S. Provisional Appln. Ser. No. 60/111,033, filed Dec. 4, 1998; and to U.S. Provisional Appln. Ser. No. 60/130,180, filed Apr. 20, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999; and to U.S. Provisional Appln. Ser. No. 60/146,904, filed Aug. 2, 1999; and to U.S. Provisional Appln. Ser. No. 60/146,907, filed Aug. 2, 1999. U.S. application Ser. No. 09/553,094 also claims the benefit of U.S. Provisional Appln. Ser. No. 60/130,178, filed Apr. 20, 1999; and to U.S. Provisional Appln. Ser. No. 60/130,180, filed Apr. 20, 1999; and to U.S. Provisional Appln. Ser. No. 60/132,860, filed May 7, 1999; and to U.S. Provisional Appln. Ser. No. 60/145,146, filed Jul. 22, 1999; and to U.S. Provisional Appln. Ser. No. 60/145,147, filed Jul. 22, 1999; and to U.S. Provisional Appln. Ser. No. 60/145,148, filed Jul. 22, 1999; and to U.S. Provisional Appln. Ser. No. 60/145,485, filed Jul. 23, 1999; and to U.S. Provisional Appln. Ser. No. 60/146,904, filed Aug. 2, 1999; and to U.S. Provisional Appln. Ser. No. 60/146,907, filed Aug. 2, 1999; and to U.S. Provisional Appln. Ser. No. 60/161,619, filed Oct. 26, 1999. U.S. application Ser. No. 09/565,306 also claims the benefit of U.S. Provisional Appln. Ser. No. 60/132,860, filed May 7, 1999; and to U.S. Provisional Appln. Ser. No. 60/146,904, filed Aug. 2, 1999; and to U.S. Provisional Appln. Ser. No. 60/146,907, filed Aug. 2, 1999; and to U.S. Provisional Appln. Ser. No. 60/161,619, filed Oct. 26, 1999; and to U.S. Provisional Appln. Ser. No. 60/179,730, filed Feb. 2, 2000. U.S. application Ser. No. 09/696,664 also claims the benefit of U.S. Provisional Appln. Ser. No. 60/161,619, filed Oct. 26, 1999; and to U.S. Provisional Appln. Ser. No. 60/207,458, filed May 30, 2000; and to U.S. Provisional Appln. Ser. No. 60/208,063, filed May 31, 2000; and to U.S. Provisional Appln. Ser. No. 60/209,830, filed Jun. 6, 2000. All of the above-listed applications are herein incorporated by reference in their entirety.

INCORPORATION OF SEQUENCE LISTING

This application contains a sequence listing, which is contained on three identical CD-ROMs: two copies of the sequence listing (Copy 1 and Copy 2) and a sequence listing Computer Readable Form (CRF), all of which are herein incorporated by reference. All three CD-ROMs each contain one file called "51721C seq list.txt" which is 13,172,736 bytes in size (measured in Windows XP) and which was created on Jan. 12, 2006.

FIELD OF THE INVENTION

The present invention is in the field of plant biochemistry. More specifically the invention relates to nucleic acid molecules that encode proteins and fragments of proteins produced in plant cells, in particular, maize plants. The invention also relates to proteins and fragments of proteins so encoded and antibodies capable of binding the proteins. The invention also relates to methods of using the nucleic acid molecules, proteins and fragments of proteins.

BACKGROUND OF THE INVENTION

I. Expressed Sequence Tag Nucleic Acid Molecules

Expressed sequence tags, or ESTs, are short sequences of randomly selected clones from a cDNA (or complementary DNA) library which are representative of the cDNA inserts of these randomly selected clones. McCombie, et al., *Nature Genetics,* 1: 124-130 (1992); Kurata, et al., *Nature Genetics,* 8: 365-372 (1994); Okubo, et al., *Nature Genetics,* 2: 173-179 (1992), all of which references are incorporated herein in their entirety.

Using conventional methodologies, cDNA libraries can be constructed from the mRNA (messenger RNA) of a given tissue or organism using poly dT primers and reverse transcriptase (Efstratiadis, et al., *Cell* 7:279-288 (1976), the entirety of which is herein incorporated by reference; Higuchi, et al., *Proc. Natl. Acad. Sci. (U.S.A.)* 73:3146-3150 (1976), the entirety of which is herein incorporated by reference; Maniatis, et al., *Cell* 8:163 (1976) the entirety of which is herein incorporated by reference; Land, et al., *Nucleic Acids Res.* 9:2251-2266 (1981), the entirety of which is herein incorporated by reference; Okayama, et al., *Mol. Cell. Biol.* 2:161-170 (1982), the entirety of which is herein incorporated by reference; Gubler, et al., *Gene* 25:263 (1983), the entirety of which is herein incorporated by reference).

Several methods may be employed to obtain full-length cDNA constructs. For example, terminal transferase can be used to add homopolymeric tails of dC residues to the free 3' hydroxyl groups (Land, et al., *Nucleic Acids Res.* 9:2251-2266 (1981), the entirety of which is herein incorporated by reference). This tail can then be hybridized by a poly dG oligo which can act as a primer for the synthesis of full length second strand cDNA. Okayama and Berg, report a method for obtaining full length cDNA constructs. This method has been simplified by using synthetic primer-adapters that have both homopolymeric tails for priming the synthesis of the first and second strands and restriction sites for cloning into plasmids (Coleclough, et al., *Gene* 34:305-314 (1985), the entirety of which is herein incorporated by reference) and bacteriophage vectors (Krawinkel, et al., *Nucleic Acids Res.* 14:1913 (1986), the entirety of which is herein incorporated by reference; and Han, et al., *Nucleic Acids Res.* 15:6304 (1987), the entirety of which is herein incorporated by reference).

These strategies have been coupled with additional strategies for isolating rare mRNA populations. For example, a typical mammalian cell contains between 10,000 and 30,000 different mRNA sequences. Davidson, *Gene Activity in Early Development*, 2nd ed., Academic Press, New York (1976). The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA. (Sambrook, et al., *Molecular Cloning: A Laboratory Manual*, 2nd ed., Cold Spring Harbor Laboratory Press (1989), the entirety of which is herein incorporated by reference.).

A method to enrich preparations of mRNA for sequences of interest is to fractionate by size. One such method is to fractionate by electrophoresis through an agarose gel (Pennica, et al., *Nature* 301:214-221 (1983), the entirety of which is herein incorporated by reference). Another such method employs sucrose gradient centrifugation in the presence of an agent, such as methylmercuric hydroxide, that denatures secondary structure in RNA (Schweinfest, et al., *Proc. Natl. Acad. Sci. (U.S.A.)* 79:4997-5000 (1982), the entirety of which is herein incorporated by reference).

A frequently adopted method is to construct equalized or normalized cDNA libraries (Ko, *Nucleic Acids Res.* 18:5705-5711 (1990), the entirety of which is herein incorporated by reference; Patanjali, S. R. et al., *Proc. Natl. Acad. Sci. (U.S.A.)* 88:1943-1947 (1991), the entirety of which is herein incorporated by reference). Typically, the cDNA population is normalized by subtractive hybridization. Schmid, et al., *J. Neurochem.* 48:307-312 (1987) the entirety of which is herein incorporated by reference; Fargnoli, et al., *Anal. Biochem.* 187:364-373 (1990) the entirety of which is herein incorporated by reference; Travis, et al., *Proc. Natl. Acad. Sci. (U.S.A.)* 85:1696-1700 (1988) the entirety of which is herein incorporated by reference; Kato, *Eur. J. Neurosci.* 2:704 (1990); and Schweinfest, et al., *Genet. Anal. Tech. Appl.* 7:64 (1990), the entirety of which is herein incorporated by reference). Subtraction represents another method for reducing the population of certain sequences in the cDNA library. Swaroop, et al., *Nucleic Acids Res.* 19:1954 (1991), the entirety of which is herein incorporated by reference).

ESTs can be sequenced by a number of methods. Two basic methods may be used for DNA sequencing, the chain termination method of Sanger et al., *Proc. Natl. Acad. Sci. (U.S.A.)* 74: 5463-5467 (1977), the entirety of which is herein incorporated by reference and the chemical degradation method of Maxam and Gilbert, *Proc. Nat. Acad. Sci. (U.S.A.)* 74: 560-564 (1977), the entirety of which is herein incorporated by reference. Automation and advances in technology such as the replacement of radioisotopes with fluorescence-based sequencing have reduced the effort required to sequence DNA (Craxton, *Methods*, 2: 20-26 (1991), the entirety of which is herein incorporated by reference; Ju et al., *Proc. Natl. Acad. Sci. (U.S.A.)* 92: 4347-4351 (1995), the entirety of which is herein incorporated by reference; Tabor and Richardson, *Proc. Natl. Acad. Sci. (U.S.A.)* 92: 6339-6343 (1995), the entirety of which is herein incorporated by reference). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, *Nucleic Acids Res.* 18:1415-1419 (1990); Smith, *Nature* 349:812-813 (1991); Luckey et al., *Methods Enzymol.* 218:154-172 (1993); Lu et al., *J. Chromatog. A.* 680:497-501 (1994); Carson et al., *Anal. Chem.* 65:3219-3226 (1993); Huang et al., *Anal. Chem.* 64:2149-2154 (1992); Kheterpal et al., *Electrophoresis* 17:1852-1859 (1996); Quesada and Zhang, *Electrophoresis* 17:1841-1851 (1996); Baba, *Yakugaku Zasshi* 117: 265-281 (1997), all of which are herein incorporated by reference in their entirety).

ESTs longer than 150 bases have been found to be useful for similarity searches and mapping. (Adams, et al., *Science* 252:1651-1656 (1991), herein incorporated by reference.) EST sequences normally range from 150-450 bases. This is the length of sequence information that is routinely and reliably generated using single run sequence data. Typically, only single run sequence data is obtained from the cDNA library, Adams, et al., *Science* 252:1651-1656 (1991). Automated single run sequencing typically results in an approximately 2-3% error or base ambiguity rate. (Boguski, et al., *Nature Genetics*, 4:332-333 (1993), the entirety of which is herein incorporated by reference).

EST databases have been constructed or partially constructed from, for example, *C. elegans* (McCombrie, et al., *Nature Genetics* 1: 124-131 (1992), human liver cell line HepG2 (Okubo, et al., *Nature Genetics* 2:173-179 (1992)), human brain RNA (Adams, et al., *Science* 252:1651-1656 (1991); Adams, et al., *Nature* 355:632-635 (1992)), *Arabidopsis*, (Newman, et al., *Plant Physiol.* 106:1241-1255 (1994)); and rice (Kurata, et al., *Nature Genetics* 8:365-372 (1994).

II. Sequence Comparisons

A characteristic feature of a protein or DNA sequence is that it can be compared with other known protein or DNA sequences. Sequence comparisons can be undertaken by determining the similarity of the test or query sequence with sequences in publicly available or propriety databases ("similarity analysis") or by searching for certain motifs ("intrinsic sequence analysis")(e.g. cis elements)(Coulson, *Trends in Biotechnology*, 12: 76-80 (1994), the entirety of which is herein incorporated by reference; Birren, et al., *Genome Analysis*, 1: 543-559 (1997), the entirety of which is herein incorporated by reference).

Similarity analysis includes database search and alignment. Examples of public databases include the DNA Database of Japan (DDBJ) (available on the Worldwide Web at ddbj.nig.ac jp/); Genebank (available on the Worldwide Web at ncbi.nlm.nih.gov/web/Genbank/Index.htlm); and the European Molecular Biology Laboratory Nucleic Acid Sequence Database (EMBL) (available on the Worldwide Web at ebi.ac.uk/ebi_docs/embl_db.html). A number of different search algorithms have been developed, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology*, 12: 76-80 (1994); Birren, et al., *Genome Analysis*, 1: 543-559 (1997)).

BLASTN takes a nucleotide sequence (the query sequence) and its reverse complement and searches them against a nucleotide sequence database. BLASTN was designed for speed, not maximum sensitivity, and may not find distantly related coding sequences. BLASTX takes a nucleotide sequence, translates it in three forward reading frames and three reverse complement reading frames, and then compares the six translations against a protein sequence database. BLASTX is useful for sensitive analysis of preliminary (single-pass) sequence data and is tolerant of sequencing errors (Gish and States, *Nature Genetics*, 3: 266-272 (1993), the entirety of which is herein incorporated by reference). BLASTN and BLASTX may be used in concert for analyzing EST data (Coulson, *Trends in Biotechnology*, 12: 76-80 (1994); Birren, et al., *Genome Analysis*, 1: 543-559 (1997).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins*, 17: 49-61 (1993), the entirety of which is herein incorporated by reference), which is currently the default choice for BLAST programs. BLOSUM62 is tailored for alignments of moderately diverged sequences and thus may not yield the best results under all conditions. Altschul, *J. Mol. Biol.* 36: 290-300 (1993), the entirety of which is herein incorporated by reference, uses a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package available that performs progressive multiple sequence alignments based on the method of Feng and Doolittle, *J. Mol. Evol.* 25: 351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices, or supply their own scoring matrix for both the pairwise alignments and the multiple alignments. CLUSTAL W for UNIX and VMS systems is available at: ftp.ebi.ac.uk. Another program is MACAW (Schuler et al., *Proteins, Struct. Func. Genet*, 9:180-190 (1991), the entirety of which is herein incorporated by reference, for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of sequence motifs in the world is PROSITE (Bairoch and Bucher, *Nucleic Acid Research*, 22: 3583-3589 (1994), the entirety of which is herein incorporated by reference.) PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by S. Henikoff, *Trends Biochem Sci.*, 18:267-268 (1993), the entirety of which is herein incorporated by reference; Henikoff and Henikoff, *Nucleic Acid Research*, 19:6565-6572 (1991), the entirety of which is herein incorporated by reference; Henikoff and Henikoff, *Proteins*, 17: 49-61 (1993). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein or nucleotide query can be submitted to the BLOCKS server; if a nucleotide sequence is submitted, the sequence is translated in all six reading frames and motifs are sought in these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches (such as GCG program ProfileSearch) and Hidden Markov Models (HMMs) (Krough et al., *J. Mol. Biol.* 235:1501-1531 (1994); Eddy, *Current Opinion in Structural Biology* 6:361-365 (1996), both of which are herein incorporated by reference in their entirety). In both cases, a large number of common protein domains have been converted into profiles, as present in the PROSITE library, or HHM models, as in the Pfam protein domain library (Sonnhammer et al., *Proteins* 28:405-420 (1997), the entirety of which is herein incorporated by reference). Pfam contains more than 500 HMM models for enzymes, transcription factors, signal transduction molecules, and structural proteins. Protein databases can be queried with these profiles or HMM models, which will identify proteins containing the domain of interest. For example, HMMSW or HMMFS, two programs in a public domain package called HMMER (Sonnhammer et al., *Proteins* 28:405-420 (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov et al. *Proc. Natl. Acad. Sci.* 91: 12091-12095 (1994), the entirety of which is herein incorporated by reference.) On the basis of an aligned set of input sequences, a weight matrix is calculated by using one of four methods (selected by the user); a weight matrix is simply a representation, position by position in an alignment, of how likely a particular amino acid will appear. The calculated weight matrix is then used to search the databases. To increase sensitivity, newly found sequences are added to the original data set, the weight matrix is recalculated, and the search is performed again. This procedure continues until no new sequences are found.

SUMMARY OF THE INVENTION

The present invention provides a substantially purified nucleic acid molecule that encodes a maize protein or fragment thereof comprising a nucleic acid sequence selected from the group consisting of SEQ ID NO: 1 through SEQ ID NO: 17472.

The present invention also provides one or more substantially purified nucleic acid molecules comprising a nucleic acid sequence selected from the group consisting of SEQ ID NO: 1 through SEQ ID NO:17472 or complements thereof.

The present invention also provides a substantially purified maize protein or fragment thereof, wherein said maize protein is encoded by a nucleic acid molecule that comprises a nucleic acid sequence selected from the group consisting of SEQ ID NO: 1 through SEQ ID NO: 17472.

The present invention further provides a substantially purified protein, peptide, or fragment thereof encoded by a nucleic acid sequence which specifically hybridizes to a nucleic acid molecule comprising a nucleic acid sequence selected from the group consisting of a complement of SEQ ID NO: 1 through SEQ ID NO: 17472.

The present invention further provides a substantially purified antibody capable of specifically binding to a protein or fragment thereof encoded by a nucleic acid sequence which specifically hybridizes to a nucleic acid molecule having a nucleic acid sequence selected from the group consisting of a complement of SEQ ID NO: 1 through SEQ ID NO: 17472.

The present invention also provides a transformed plant transformed to contain a nucleic acid molecule which comprises: (A) an exogenous promoter region which functions in plant cells to cause the production of an mRNA molecule; which is linked to (B) a structural nucleic acid molecule, wherein said structural nucleic acid molecule comprises a nucleic acid molecule that encodes a protein, peptide, or fragment thereof which hybridizes to a nucleic acid sequence selected from the group consisting of a complement of SEQ ID NO: 1 through SEQ ID NO: 17472 expressed in an effective amount to produce a desirable agronomic effect; which is linked to (C) a 3' non-translated sequence that functions in plant cells to cause the termination of transcription and the addition of polyadenylated ribonucleotides to the 3' end of the mRNA sequence.

The present invention also provides a transformed plant cell containing a nucleic acid molecule whose non-transcribed strand encodes a protein or fragment thereof, wherein the transcribed strand of said nucleic acid is complementary to a nucleic acid molecule that encodes a protein or fragment thereof. The present invention also provides bacterial, viral, microbial, and plant cells comprising a nucleic acid molecule of the present invention The present invention also provides a method of producing a plant containing one or more proteins encoded by sequences comprising SEQ ID NO:1 or complement thereof through SEQ ID NO:17472 or complements thereof, expressed in a sufficient amount and/or fashion to produce a desirable agronomic effect.

In accomplishing the foregoing, there is provided, in accordance with one aspect of the present invention, methods of producing genetically transformed plants, comprising the steps of:

(a) inserting into the genome of a plant cell a recombinant, double-stranded DNA molecule comprising
  (i) a promoter which functions in plant cells to cause the production of an RNA sequence,
  (ii) a structural DNA sequence that causes the production of an RNA sequence which encodes a desired protein.
  (iii) a 3' non-translated DNA sequence which functions in plant cells to cause the addition of polyadenylated nucleotides to the 3' end of RNA sequence; where the promoter is homologous or heterologous with respect to the coding sequence and adapted to cause sufficient expression of a protein in desired plant tissues to enhance the agronomic utility of a plant transformed with said gene.
(b) obtaining a transformed plant cell with said nucleic acid molecule that encodes one or more proteins, wherein said nucleic acid molecule is transcribed and results in expression of said protein(s); and
(c) regenerating from the transformed plant cell a genetically transformed plant The present invention also encompasses differentiated plants, seeds, and progeny comprising said transformed plant cells and which exhibit novel properties of agronomic significance.

The present invention also provides a method of producing a plant containing reduced levels of a protein comprising: (A) transforming a plant cell with a nucleic acid molecule that encodes a protein, wherein said nucleic acid molecule is transcribed and results in co-suppression of endogenous protein synthesis activity, and (B) regenerating plants and producing subsequent progeny from the transformed plant.

The present invention also provides a method of determining an association between a polymorphism and a plant trait comprising: (A) hybridizing a nucleic acid molecule specific for a polymorphism to genetic material of a plant, wherein said nucleic acid molecule comprising a nucleic acid sequence selected from the group consisting of SEQ ID NO:

1 through SEQ ID NO:17472 or complements thereof; and (B) calculating the degree of association between the polymorphism and the plant trait.

The present invention also provides a method of isolating a genetic region, or nucleic acid that encodes a protein or fragment thereof comprising: (A) incubating under conditions permitting nucleic acid hybridization: a marker nucleic acid molecule, preferably an EST, with a complementary nucleic acid molecule obtained from a plant cell or plant tissue; (B) permitting hybridization between said marker nucleic acid molecule, preferably an EST, and said complementary nucleic acid molecule obtained from said plant cell or plant tissue; and (C) isolating said complementary nucleic acid molecule.

The present invention also provides a method for determining a level or pattern in a plant cell of a protein in a plant comprising: (A) incubating, under conditions permitting nucleic acid hybridization, a marker nucleic acid molecule, the marker nucleic acid molecule selected from the group of marker nucleic acid molecules which specifically hybridize to a nucleic acid molecule having the nucleic acid sequence selected from the group consisting of SEQ ID NO: 1 through SEQ ID NO: 17472 or complements thereof or fragments of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of an mRNA for the enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the protein.

The present invention also provides a method for determining the level or pattern of a protein in a plant cell or plant tissue comprising: (A) incubating under conditions permitting nucleic acid hybridization: a marker nucleic acid molecule, the marker nucleic acid molecule comprising a nucleotide sequence selected from the group consisting of SEQ ID NO: 1 through SEQ ID NO:17472 or complements thereof, with a complementary nucleic acid molecule obtained from a plant cell or plant tissue, wherein nucleic acid hybridization between the marker nucleic acid molecule, and the complementary nucleic acid molecule obtained from the plant cell or plant tissue permits the detection of said protein; (B) permitting hybridization between the marker nucleic acid molecule and the complementary nucleic acid molecule obtained from the plant cell or plant tissue; and (C) detecting the level or pattern of the complementary nucleic acid, wherein the detection of said complementary nucleic acid is predictive of the level or pattern of the protein synthesis.

The present invention also provides a method for determining a level or pattern of a protein in a plant cell or plant tissue which comprises assaying the concentration of a molecule, whose concentration is dependent upon the expression of a gene, the gene having a nucleic acid sequence which specifically hybridizes to a protein marker nucleic acid molecule, the molecule being present in a plant cell or plant tissue, in comparison to the concentration of that molecule present in a plant cell or plant tissue with a known level or pattern of said protein, wherein an assayed concentration of the molecule is compared to the assayed concentration of the molecule in a plant cell or plant tissue with a known level or pattern of said protein.

The present invention also provides a method of determining a mutation in a plant whose presence is predictive of a mutation affecting a level or pattern of a protein comprising the steps: (A) incubating, under conditions permitting nucleic acid hybridization, a marker nucleic acid, the marker nucleic acid selected from the group of marker nucleic acid molecules which specifically hybridize to a nucleic acid molecule consisting of the nucleic acid sequence selected from the group consisting of SEQ ID NO: 1 through SEQ ID NO: 17472 or complements thereof or fragments of either and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of protein synthesis comprising the steps: (A) incubating under conditions permitting nucleic acid hybridization: a marker nucleic acid molecule, the marker nucleic acid molecule comprising a nucleic acid molecule that is linked to gene, the gene having a nucleic acid sequence which specifically hybridizes to a sequence selected from the group consisting of SEQ ID NO: 1 through SEQ ID NO:17472 and complements thereof, and a complementary nucleic acid molecule obtained from a plant tissue or plant cell of the plant, wherein nucleic acid hybridization between the marker nucleic acid molecule and the complementary nucleic acid molecule obtained from the plant permits the detection of a polymorphism whose presence is predictive of a mutation affecting said level or pattern of a protein synthesis in the plant; (B) permitting hybridization between said marker nucleic acid molecule and said complementary nucleic acid molecule obtained from said plant; and; (C) detecting the presence of the polymorphism, wherein the detection of the polymorphism is predictive of the mutation.

The present invention also provides a method for reducing expression of a protein in a plant cell, the method comprising: growing a transformed plant cell containing a nucleic acid molecule whose non-transcribed strand encodes a protein or fragment thereof, wherein the transcribed strand of said nucleic acid is complementary to a nucleic acid molecule that encodes the protein in said plant cell, and whereby the strand that is complementary to the nucleic acid molecule that encodes the protein reduces or depresses expression of the protein.

The present invention provides maize nucleic acid molecules for use as molecular tags to isolate genetic regions (i.e. promoters and flanking sequences), isolate genes, map genes, and determine gene function. The present invention further provides maize nucleic acid molecules for use in determining if genes are members of a particular gene family.

The present invention also provides a method of obtaining full length genes using maize ESTs or complements thereof or fragments of either.

The present invention also provides a method of isolating promoters and flanking sequences using maize ESTs or complements thereof or fragments of either.

The present invention also provides maize ESTs or complements thereof or fragments of either for use in marker-assisted breeding programs.

The present invention also provides a method of identifying tissues comprising hybridizing nucleic acids from the tissue with maize ESTs or complements thereof or fragments of either.

The present invention also provides a method for production of antibodies targeted against the proteins, peptides, or fragments produced by the disclosed or complements thereof or fragments of either.

The present invention also provides a method for the transformation and regeneration of plants comprising sequences hybridizable to the disclosed ESTs or complements thereof or fragments of either.

The present invention also provides a method of modifying plant protein expression by inserting in a chimeric gene sense or antisense constructs of the maize ESTs.

DETAILED DESCRIPTION OF THE INVENTION

Agents
  (a) Nucleic Acid Molecules

Agents of the present invention include nucleic acid molecules and more specifically EST nucleic acid molecules or nucleic acid fragment molecules thereof. Fragment EST nucleic acid molecules may encode significant portion(s) of, or indeed most of, the EST nucleic acid molecule. Alternatively, the fragments may comprise smaller oligonucleotides (having from about 15 to about 250 nucleotide residues, and more preferably, about 15 to about 30 nucleotide residues).

A subset of the nucleic acid molecules of the present invention includes nucleic acid molecules that are marker molecules. Another subset of the nucleic acid molecules of the present invention include nucleic acid molecules that encode a protein or fragment thereof. Another subset of the nucleic acid molecules of the present invention are EST molecules.

The term "substantially purified", as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant, refers to a) molecules that are constructed outside of living cells by joining natural or synthetic DNA segments to DNA molecules that can replicate in a living cell or b) molecules that result from the replication or expression of those molecules described above or c) amino acid molecules from different sources which are joined together.

It is understood that the agents of the present invention may be labeled with reagents that facilitate detection of the agent (e.g. fluorescent labels (Prober, et al., *Science* 238:336-340 (1987); Albarella et al., EP 144914, chemical labels (Sheldon et al., U.S. Pat. No. 4,582,789; Albarella et al., U.S. Pat. No. 4,563,417, modified bases (Miyoshi et al., EP 119448, all of which are hereby incorporated by reference in their entirety).

It is further understood, that the present invention provides bacterial, viral, microbial, and plant cells comprising the agents of the present invention.

Nucleic acid molecules or fragment thereof of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, et al., In: *Molecular Cloning, A Laboratory Manual, 2nd Edition*, Cold Spring Harbor Press, Cold Spring Harbor, N.Y. (1989), and by Haymes, et al. In: *Nucleic Acid Hybridization, A Practical Approach*, IRL Press, Washington, D.C. (1985), the entirety of which is herein incorporated by reference. Departures from complete complementarity are therefore permissible, as long as such departures do not completely preclude the capacity of the molecules to form a double-stranded structure. Thus, in order for an nucleic acid molecule or fragment of the present invention to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 17472 or complements thereof under moderately stringent conditions, for example, at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO:1 through SEQ ID NO: 17472 or complements thereof under high stringency conditions.

In one aspect of the present invention, the nucleic acid molecules of the present invention have one or more of the nucleic acid sequences set forth in SEQ ID NO: 1 through SEQ ID NO:17472 or complements thereof. In another aspect of the present invention, one or more of the nucleic acid molecules of the present invention share between 100% and 90% sequence identity with one or more of the nucleic acid sequences set forth in SEQ ID NO: 1 through SEQ ID NO:17472 or complements thereof. In a further aspect of the present invention, one or more of the nucleic acid molecules of the present invention share between 100% and 95% sequence identity with one or more of the nucleic acid sequences set forth in SEQ ID NO: 1 through SEQ ID NO:17472 or complements thereof. In a more preferred aspect of the present invention, one or more of the nucleic acid molecules of the present invention share between 100% and 98% sequence identity with one or more of the nucleic acid sequences set forth in SEQ ID NO: 1 through SEQ ID NO:17472 or complements thereof. In an even more preferred aspect of the present invention, one or more of the nucleic acid molecules of the present invention share between 100% and 99% sequence identity with one or more of the sequences set forth in SEQ ID NO: 1 through SEQ ID NO:17472 or complements thereof. In a further, even more preferred aspect of the present invention, one or more of the nucleic acid molecules of the present invention exhibit 100% sequence identity with one or more nucleic acid molecules present within the cDNA libraries designated LIB3179, LIB3227, LIB3228, and LIB3279 (Monsanto Company, St. Louis, Mo., United States of America).

The term "sequence identity" refers to the extent to which two sequences, nucleotide or amino acid, are invariant throughout the portion at which they are aligned. While there exist a number of methods to measure identity between two polynucleotide or polypeptide sequences, the term "sequence identity" is well known to skilled artisans. Methods commonly employed to determine identity between two sequences include, but are not limited to, those disclosed in *Guide to Huge Computers*, Martin J. Bishop, ed., Academic Press, San Diego, 1994, and Carillo, H., and Lipton, D.; Siam, *J Applied Math* (1988) 48:1073. Methods to determine identity are codified in computer programs. Preferred computer program methods to determine identity between two sequences include, but are not limited to, the BLAST suite of programs publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403-410 (1990), Pearson et al., Proc. Natl. Acad. Sci. U.S.A. 85:2444-2448 (1988), the FAST programs (Pearson et al., *Proc. Natl. Acad. Sci. U.S.A.* 85:2444-2448 (1988). the GAP and BESTFIT programs found in the GCG program package, (Madison, Wis.) and Cross_Match (Phi Green, University of Washington). Another preferred method to determine identity, is by the method of DNASTAR protein alignment protocol using the Jotun-Hein algorithm (Hein et al., *Methods Enzymol.* 183: 626-645 (1990)).

In a preferred embodiment of the present invention, a maize protein or fragment thereof of the present invention is a homologue of another plant protein. In another preferred embodiment of the present invention, a maize protein or fragment thereof of the present invention is a homologue of a fungal protein. In another preferred embodiment of the present invention, a maize protein or fragment thereof of the present invention is a homologue of a mammalian protein. In another preferred embodiment of the present invention, a maize protein or fragment thereof of the present invention is a homologue of an algal protein. In another preferred embodiment of the present invention, a maize protein or fragment thereof of the present invention is a homologue of a bacterial protein. In another preferred embodiment of the present invention, a maize protein or fragment thereof of the present invention is a homologue of a soybean protein. In another preferred embodiment of the present invention, a maize protein or fragment thereof of the present invention is a homologue of a cotton protein. In another preferred embodiment of the present invention, a maize protein or fragment thereof of the present invention is a homologue of a wheat protein.

In a preferred embodiment of the present invention, the nucleic molecule of the present invention encodes a maize protein or fragment thereof where a maize protein or fragment thereof exhibits a BLAST probability score of greater than 1E-12, preferably a BLAST probability score of between about 1E-30 and about 1E-12, even more preferably a BLAST probability score of greater than 1E-30 with its homologue.

In another preferred embodiment of the present invention, the nucleic acid molecule encoding a maize protein or fragment thereof exhibits a % identity with its homologue of between about 25% and about 40%, more preferably of between about 40% and about 70%, even more preferably of between about 70% and about 90% and even more preferably between about 90% and 99%. In another preferred embodiment, of the present invention, a maize protein or fragment thereof exhibits a % identity with its homologue of 100%.

In a preferred embodiment of the present invention, the nucleic acid molecule of the present invention encodes a maize protein or fragment thereof where the maize protein exhibits a BLAST score of greater than 120, preferably a BLAST score of between about 1450 and about 120, even more preferably a BLAST score of greater than 1450 with its homologue.

Nucleic acid molecules of the present invention also include non-maize homologues. Preferred non-maize homologues are selected from the group consisting of alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, soybean, strawberry, sugarcane, sugarbeet, tomato, wheat, poplar, pine, fir, eucalyptus, apple, lettuce, lentils, grape, banana, tea, turf grasses, sunflower, oil palm and *Phaseolus*.

The degeneracy of the genetic code, which allows different nucleic acid sequences to code for the same protein or peptide, is known in the literature. (U.S. Pat. No. 4,757,006, the entirety of which is herein incorporated by reference).

In an aspect of the present invention, one or more of the nucleic acid molecules of the present invention differ in nucleic acid sequence from those encoding a maize protein or fragment thereof in SEQ ID NO: 1 through SEQ ID NO: 17472 due to the degeneracy in the genetic code in that they encode the same protein but differ in nucleic acid sequence.

In another further aspect of the present invention, nucleic acid molecules of the present invention can comprise sequences, which differ from those encoding a protein or fragment thereof in SEQ ID NO: 1 through SEQ ID NO: 17472 due to fact that the different nucleic acid sequence encodes a protein having one or more conservative amino acid changes. It is understood that codons capable of coding for such conservative amino acid substitutions are known in the art.

It is well known in the art that one or more amino acids in a native sequence can be substituted with another amino acid(s), the charge and polarity of which are similar to that of the native amino acid, i.e., a conservative amino acid substitution, resulting in a silent change. Conserved substitutes for an amino acid within the native polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid changes within the native polypeptides sequence can be made by substituting one amino acid within one of these groups with another amino acid within the same group. Biologically functional equivalents of the proteins or fragments thereof of the present invention can have 10 or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigent-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, obtain a protein with like properties. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105-132 (1982), herein incorporated by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference in its entirety, states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those which are within ±1 are particularly preferred, and those within ±0.5 are even more particularly preferred.

In a further aspect of the present invention, one or more of the nucleic acid molecules of the present invention differ in nucleic acid sequence from those encoding a maize protein or fragment thereof set forth in SEQ ID NO: 1 through SEQ ID NO: 17472 or fragment thereof due to the fact that one or more codons encoding an amino acid has been substituted for a codon that encodes a nonessential substitution of the amino acid originally encoded.

One aspect of the present invention concerns markers that include nucleic acid molecules SEQ ID NO: 1 through SEQ ID NO: 17472 or complements thereof or fragments of either that can act as markers or other nucleic acid molecules of the present invention that can act as markers. Genetic markers of the present invention include "dominant" or "codominant" markers "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g. absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

SNPs are single base changes in genomic DNA sequence. They occur at greater frequency and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a results of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980), the entirety of which is herein incorporated reference; Konieczny and Ausubel, *Plant J.* 4:403-410 (1993), the entirety of which is herein incorporated by reference), enzymatic and chemical mismatch assays (Myers et al., *Nature* 313:495-498 (1985), the entirety of which is herein incorporated by reference), allele-specific PCR (Newton et al., *Nucl. Acids Res.* 17:2503-2516 (1989), the entirety of which is herein incorporated by reference; Wu et al., *Proc. Natl. Acad. Sci. (U.S.A.)* 86:2757-2760 (1989), the entirety of which is herein incorporated by reference), ligase chain reaction (Barany, *Proc. Natl. Acad. Sci. (U.S.A.)* 88:189-193 (1991), the entirety of which is herein incorporated by reference), single-strand conformation polymorphism analysis (Labrune et al., *Am. J. Hum. Genet.* 48: 1115-1120 (1991), the entirety of which is herein incorporated by reference), primer-directed nucleotide incorporation assays (Kuppuswami et al., *Proc. Natl. Acad. Sci. USA* 88:1143-1147 (1991), the entirety of which is herein incorporated by reference), dideoxy fingerprinting (Sarkar et al., *Genomics* 13:441-443 (1992), the entirety of which is herein incorporated by reference), solid-phase ELISA-based oligonucleotide ligation assays (Nikiforov et al., *Nucl. Acids Res.* 22:4167-4175 (1994), the entirety of which is herein incorporated by reference), oligonucleotide fluorescence-quenching assays (Livak et al., *PCR Methods Appl.* 4:357-362 (1995), the entirety of which is herein incorporated by reference), 5'-nuclease allele-specific hybridization TaqMan assay (Livak et al., *Nature Genet.* 9:341-342 (1995), the entirety of which is herein incorporated by reference), template-directed dye-terminator incorporation (TDI) assay (Chen and Kwok, *Nucl. Acids Res.* 25:347-353 (1997), the entirety of which is herein incorporated by reference), allele-specific molecular beacon assay (Tyagi et al., *Nature Biotech.* 16: 49-53 (1998), the entirety of which is herein incorporated by reference), PinPoint assay (Haff and Smirnov, *Genome Res.* 7: 378-388 (1997), the entirety of which is herein incorporated by reference) and dCAPS analysis (Neff et al., *Plant J.* 14:387-392 (1998), the entirety of which is herein incorporated by reference).

Additional markers, such as AFLP markers, RFLP markers and RAPD markers, can be utilized (Walton, *Seed World* 22-29 (July, 1993), the entirety of which is herein incorporated by reference; Burow and Blake, *Molecular Dissection of Complex Traits*, 13-29, Paterson (ed.), CRC Press, New York (1988), the entirety of which is herein incorporated by reference). DNA markers can be developed from nucleic acid molecules using restriction endonucleases, the PCR and/or DNA sequence information. RFLP markers result from single base changes or insertions/deletions. These codominant markers are highly abundant in plant genomes, have a medium level of polymorphism and are developed by a combination of restriction endonuclease digestion and Southern blotting hybridization. CAPS are similarly developed from restriction nuclease digestion but only of specific PCR products. These markers are also codominant, have a medium level of polymorphism and are highly abundant in the genome. The CAPS result from single base changes and insertions/deletions.

Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant are highly abundant in genomes and exhibit a medium level of polymorphism.

SSRs require DNA sequence information. These codominant markers result from repeat length changes, are highly polymorphic and do not exhibit as high a degree of abundance in the genome as CAPS, AFLPs and RAPDs. SNPs also require DNA sequence information. These codominant markers result from single base substitutions. They are highly abundant and exhibit a medium of polymorphism (Rafalski et al., In: *Nonmammalian Genomic Analysis*, Birren and Lai (ed.), Academic Press, San Diego, Calif., pp. 75-134 (1996), the entirety of which is herein incorporated by reference). It is understood that a nucleic acid molecule of the present invention may be used as a marker.

A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (available on the Worldwide Web at genome.wi.mit.edu/cgi-bin/primer/primer3.cgi), STSPipeline (available on the Worldwide Web at genome.wi.mit.edu/cgi-bin/www-STS_Pipeline), or GeneUp (Pesole et al., *BioTechniques* 25:112-123 (1998) the entirety of which is herein incorporated by reference), for example, can be used to identify potential PCR primers.

It is understood that a fragment of one or more of the nucleic acid molecules of the present invention may be a probe and specifically a PCR probe.

(b) Protein and Peptide Molecules

A class of agents comprises one or more of the protein or peptide molecules encoded by SEQ ID NO: 1 through SEQ ID NO:17472 or one or more of the protein or fragment thereof or peptide molecules encoded by other nucleic acid agents of the present invention. As used herein, the term "protein molecule" or "peptide molecule" includes any molecule that comprises five or more amino acids. It is well know in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, homocysteine, and homoserine.

One or more of the protein or fragment of peptide molecules may be produced via chemical synthesis, or more preferably, by expression in a suitable bacterial or eukaryotic host. Suitable methods for expression are described by Sambrook, et al., (In: *Molecular Cloning, A Laboratory Manual, 2nd Edition, Cold Spring Harbor Press*, Cold Spring Harbor, N.Y. (1989)), or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecule of the present invention are preferably produced via recombinant means.

Another class of agents comprise protein or peptide molecules encoded by SEQ ID NO: 1 through SEQ ID NO:17472 or complements thereof or, fragments or fusions thereof in which non-essential, or not relevant, amino acid residues have been added, replaced, or deleted. An example of such a homologue is the homologue protein of all non-maize plant species, including but not limited to alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, soybean, strawberry, sugarcane, sugarbeet, tomato, wheat, poplar, pine, fir, eukalyptus, apple, lettuce, peas, lentils, grape, banana, tea, turf grasses, etc. Particularly preferred non-maize plants to utilize for the isolation of homologues would include alfalfa, *Arabidopsis*, barley, cotton, oat, oilseed rape, rice, canola, ornamentals, soybean, sugarcane, sugarbeet, tomato, potato, wheat, and turf grasses. Such a homologue can be obtained by any of a variety of methods. Most preferably, as indicated above, one or more of the disclosed sequences (SEQ ID NO: 1 through SEQ ID NO:17472 or complements thereof) will be used to define a pair of primers that may be used to isolate the homologue-encoding nucleic acid molecules from any desired species. Such molecules can be expressed to yield homologues by recombinant means.

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal, and may comprise intact immunoglobulins, or antigen binding portions of immunoglobulins (such as (F(ab'), F(ab')$_2$) fragments, or single-chain immunoglobulins producible, for example, via recombinant means). It is understood that practitioners are familiar with the standard resource materials which describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y. (1988), the entirety of which is herein incorporated by reference).

Murine monoclonal antibodies are particularly preferred. BALB/c mice are preferred for this purpose, however, equivalent strains may also be used. The animals are preferably immunized with approximately 25 μg of purified protein (or fragment thereof) that has been emulsified a suitable adjuvant (such as TiterMax adjuvant (Vaxcel, Norcross, Ga.)). Immunization is preferably conducted at two intramuscular sites, one intraperitoneal site, and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-protein or peptide antibodies. Preferably, a direct binding Enzyme-Linked Immunoassay (ELISA) is employed for this purpose.

More preferably, the mouse having the highest antibody titer is given a third i.v. injection of approximately 25 μg of the same protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs), preferably by direct ELISA.

In one embodiment, anti-protein or peptide monoclonal antibodies are isolated using a fusion of a protein, protein fragment, or peptide of the present invention, or conjugate of a protein, protein fragment, or peptide of the present invention, as immunogens. Thus, for example, a group of mice can be immunized using a fusion protein emulsified in Freund's complete adjuvant (e.g. approximately 50 μg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding the protein or peptide can also be obtained using this method.

In a preferred procedure for obtaining monoclonal antibodies, the spleens of the above-described immunized mice are removed, disrupted, and immune splenocytes are isolated over a ficoll gradient. The isolated splenocytes are fused, using polyethylene glycol with BALB/c-derived HGPRT (hypoxanthine guanine phosphoribosyl transferase) deficient P3×63xAg8.653 plasmacytoma cells. The fused cells are plated into 96-well microtiter plates and screened for hybridoma fusion cells by their capacity to grow in culture medium supplemented with hypothanthine, aminopterin and thymidine for approximately 2-3 weeks.

Hybridoma cells that arise from such incubation are preferably screened for their capacity to produce an immunoglobulin that binds to a protein of interest. An indirect ELISA may be used for this purpose. In brief, the supernatants of hybridomas are incubated in microtiter wells that contain immobilized protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbors. Desirably, the fusion plates are screened several times since the rates of hybridoma growth vary. In a preferred sub-embodiment, a different antigenic form of immunogen may be used to screen the hybridoma. Thus, for example, the splenocytes may be immunized with one immunogen, but the resulting hybridomas can be screened using a different immunogen. It is understood that any of the protein or peptide molecules of the present invention may be used to raise antibodies.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

Uses of the Agents of the Invention

The nucleic acid molecules and fragments thereof of the present invention from the cDNA library LIB3179 are isolated from jasmonic acid treated maize leaf tissue. Jasmonic acid plays a role in the response of plants to wounding and other stresses. It is one of signal compounds responsible for induction of pathogenesis-related (PR) proteins which show strong antifungal and antimicrobial activities. Therefore, the cDNA library of the present invention can enable acquisition of, including but not limited to, stress response genes and genes that regulate PR proteins. The ESTs of the present invention can also be used in isolating genes which would be involved in pathways, including but not limited to, of light and dark respiration, of $CO_2$ assimilation, and of nitrogen metabolism linked to fruiting and mobilization and distribution of nitrogen. Leaves are the main photosynthetic organs of crop plants, therefore, the ESTs of the present invention will find great use in the isolation of a variety of agronomically significant genes, including but not limited to, genes that regulate photosynthesis and respiration. Such genes are associated with plant growth, quality and yield, and could also serve as links in important developmental, metabolic, and catabolic pathways. Libraries from this tissue can enable the acquisition of a variety of agronomically significant genes involved in the synthesis and catabolism of commercially important traits. The ESTs of the present invention also can enable the acquisition of promoters and cis-regulatory elements which will be useful to express agronomically significant genes in these tissues and/or other tissues. The ESTs of the present invention also can enable the acquisition of molecular markers, which can be used in, including but not limited to, breeding schemes, genetic and molecular mapping, and cloning of agronomically significant genes.

The nucleic acid molecules and fragments thereof of the present invention from the subtractive cDNA library LIB3227 is generated from maize immature ear tissue, which is harvested from eight week old plants grown in a greenhouse. Libraries from this tissue can enable the acquisition of a variety of agronomically significant genes involved in the synthesis and catabolism of commercially important traits. The ESTs of the present invention can enable the acquisition of, including but are not limited to, non-regulatory genes and genes that regulate protein, oils, amino acids, sterols, minerals, isoflavones, saponins, vitamins, tocopherols, antinutrient components, carbohydrates, starch metabolism and seed regulatory elements. Such genes are associated with plant growth, quality and yield, and could also serve as links in important developmental, metabolic, and catabolic pathways. The ESTs of the present invention also can enable the acquisition of promoters and cis-regulatory elements which will be useful to express agronomically significant genes in these tissues and/or other tissues. The ESTs of the present invention also can enable the acquisition of molecular markers, which can be used in, including but not limited to, breeding schemes, genetic and molecular mapping, and cloning of agronomically significant genes.

The nucleic acid molecules and fragments thereof of the present invention from the subtractive cDNA library LIB3228 is generated from maize microspore tissue. Libraries from this tissue can enable the acquisition of a variety of agronomically significant genes involved in the synthesis and catabolism of commercially important traits. The ESTs of the present invention can enable the acquisition of, but are not limited to genes involved in reproduction, meiosis, and cell division. Such genes are associated with plant growth, quality and yield, and could also serve as links in important developmental, metabolic, and catabolic pathways. The ESTs of the present invention also can enable the acquisition of promoters and cis-regulatory elements which will be useful to express agronomically significant genes in these tissues and/or other tissues. The ESTs of the present invention also can enable the acquisition of molecular markers, which can be used in, including but not limited to, breeding schemes, genetic and molecular mapping, and cloning of agronomically significant genes.

The nucleic acid molecules and fragments thereof of the present invention from the cDNA library LIB3279 is generated from maize anthers (about 1 to 2 cm), which are harvested from greenhouse-grown plants 37 days after germination. The ESTs of the present invention can enable the acquisition of, but are not limited to genes involved in reproduction, pollen production and development, and seed production, therefore, the ESTs of the present invention will find great use in the isolation of a variety of agronomically significant genes, including but not limited to, genes that regulate microsporogenesis, meiosis, cell division, carotenoids, floral biogenesis, embryogenesis, protein, amino acids, sterols, oils, minerals, isoflavones, saponins, vitamins, tocopherols, antinutrient components, carbohydrates, starch metabolism and seed regulatory elements. Such genes are associated with plant growth, quality and yield, and could also serve as links in important developmental, metabolic, and catabolic pathways. Libraries from this tissue can enable the acquisition of a variety of agronomically significant genes involved in the synthesis and catabolism of commercially important traits. The ESTs of the present invention also can enable the acquisition of promoters and cis-regulatory elements which will be useful to express agronomically significant genes in these tissues and/or other tissues. The ESTs of the present invention also can enable the acquisition of molecular markers, which can be used in, including but not limited to, breeding schemes, genetic and molecular mapping, and cloning of agronomically significant genes.

Nucleic acid molecules and fragments thereof of the present invention may be employed to obtain other nucleic acid molecules. Such molecules include the nucleic acid molecules of other plants or other organisms (e.g., alfalfa, rice, potato, cotton, oat, rye, barley, soybean, wheat, *Arabidopsis*, *Brassica*, etc.) including the nucleic acid molecules that encode, in whole or in part, protein homologues of other plant species or other organisms, and sequences of genetic elements such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homologue molecules may differ in their nucleotide sequences from those found in one or more of SEQ ID NO:1 through SEQ ID NO:17472 or complements thereof because complete complementarity is not needed for stable hybridization. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143-4146 (1986), the entirety of which is herein incorporated by reference; Goodchild et al., *Proc. Natl. Acad. Sci. (U.S.A.)* 85:5507-5511 (1988), the entirety of which is herein incorporated by reference; Wickstrom et al., *Proc. Natl. Acad. Sci. (U.S.A.)* 85:1028-1032 (1988), the entirety of which is herein incorporated by reference; Holt, et al., *Molec. Cell. Biol.* 8:963-973 (1988), the entirety of which is herein incorporated by reference; Gerwirtz, et al., *Science* 242:1303-1306 (1988), the entirety of which is herein incorporated by reference; Anfossi, et al., *Proc. Natl. Acad. Sci. (U.S.A.)* 86:3379-3383 (1989), the entirety of which is herein incorporated by reference; Becker, et al., *EMBO J.* 8:3685-3691 (1989); the entirety of which is herein incorporated by reference). Automated nucleic acid synthesizers may be employed for this purpose. In lieu of such synthesis, the disclosed nucleic acid molecules may be used to define a pair of primers that can be used with the polymerase chain reaction (Mullis, et al., *Cold Spring Harbor Symp. Quant. Biol.* 51:263-273 (1986); Erlich et al., EP 50,424; EP 84,796; EP 258,017, EP 237,362; Mullis, EP 201,184; Mullis et al., U.S. Pat. No. 4,683,202; Erlich, U.S. Pat. No. 4,582,788; and Saiki, R. et al., U.S. Pat. No. 4,683,194, all of which are hereby incorporated by reference in their entirety) to amplify and obtain any desired nucleic acid molecule or fragment.

Promoter sequence(s) and other genetic elements including but not limited to transcriptional regulatory elements associated with one or more of the disclosed nucleic acid sequences can also be obtained using the disclosed nucleic acid sequences provided herein.

In one embodiment, such sequences are obtained by incubating EST nucleic acid molecules or preferably fragments thereof with members of genomic libraries (e.g. maize and soybean) and recovering clones that hybridize to the EST nucleic acid molecule or fragment thereof. In a second embodiment, methods of "chromosome walking," or inverse PCR may be used to obtain such sequences (Frohman, et al., *Proc. Natl. Acad. Sci. (U.S.A.)* 85:8998-9002 (1988); Ohara, et al., *Proc. Natl. Acad. Sci. (U.S.A.)* 86: 5673-5677 (1989); Pang et al., *Biotechniques,* 22(6); 1046-1048 (1977); Huang et al., *Methods Mol. Biol.* 69: 89-96 (1977); Hartl et al., *Methods Mol. Biol.* 58: 293-301 (1996), all of which are hereby incorporated by reference in their entirety). In one embodiment, the disclosed nucleic acid molecules are used to identify cDNAs whose analogous genes contain promoters with desirable expression patterns. The nucleic acid molecules isolated from the library of the present invention are used to isolate promoters of tissue-enhanced, tissue-specific, developmentally- or environmentally-regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See for example Birren et al., *Genome Analysis: Analyzing DNA,* 1, (1997), Cold Spring Harbor Laboratory Press, Cold Spring Harbor, N.Y., the entirety of which is herein incorporated by reference).

Promoters obtained utilizing the nucleic acid molecules of the present invention could also be modified to affect their control characteristics. Examples of such modifications would include but are not limited to enhancer sequences as reported by Kay et al., *Science* 236:1299 (1987), herein incorporated by reference in its entirety. Such genetic elements could be used to enhance gene expression of new and existing traits for crop improvements.

The nucleic acid molecules of the present invention may be used to isolate promoters of tissue enhanced, tissue specific, cell-specific, cell-type, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et. al., *Genome Analysis: Analyzing DNA,* 1, Cold Spring Harbor Laboratory Press, Cold Spring Harbor, N.Y. (1997), the entirety of which is herein incorporated by reference). Promoters obtained utilizing the nucleic acid molecules of the present invention could also be modified to affect their control characteristics. Examples of such modifications would include but are not limited to enhancer sequences as reported by Kay, et al *Science* 236:1299 (1987), herein incorporated reference in its entirety. Such genetic elements could be used to enhance gene expression of new and existing traits for crop improvements.

In an aspect of the present invention, one or more of the nucleic molecules of the present invention are used to determine whether a plant (preferably maize) has a mutation affecting the level (i.e., the concentration of mRNA in a sample, etc.) or pattern (i.e., the kinetics of expression, rate of decomposition, stability profile, etc.) of the expression encoded in part or whole by one or more of the nucleic acid molecules of the present invention (collectively, the "Expression Response" of a cell or tissue). As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance, male sterility, yield, quality improvements, etc.). A change in genotype or phenotype may be transient or permanent. Also as used herein, a tissue sample is any sample that comprises more than one cell. In a preferred aspect, a tissue sample comprises cells that share a common characteristic (e.g. derived from leaf, root, or pollen etc).

In one sub-aspect, such an analysis is conducted by determining the presence and/or identity of polymorphism(s) by one or more of the nucleic acid molecules of the present invention and more specifically, one or more of the EST nucleic acid molecules or fragments thereof which are associated with phenotype, or a predisposition to phenotype.

Any of a variety of molecules can be used to identify such polymorphism(s). In one embodiment, one or more of the EST nucleic acid molecules (or a sub-fragment thereof) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s), and more preferably within 100 kb of the polymorphism(s), and most preferably within 10 kb of the polymorphism(s) can be employed.

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist, and the polymorphism is thus said to be di-allelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour, et al., *FEBS Lett.* 307:113-115 (1992); Jones, et al., *Eur. J. Haematol.* 39:144-147 (1987); Horn, et al., PCT Application WO91/14003; Jeffreys, European Patent Application 370,719; Jeffreys, U.S. Pat. No. 5,699,082; Jeffreys. et al., *Amer. J. Hum. Genet.* 39:11-24 (1986); Jeffreys. et al., *Nature* 316:76-79 (1985); Gray, et al., *Proc. R. Acad. Soc. Lond.* 243:241-253 (1991); Moore, et al., *Genomics* 10:654-660 (1991); Jeffreys, et al., *Anim. Genet.* 18:1-15 (1987); Hillel, et al., *Anim. Genet.* 20:145-155 (1989); Hillel, et al., *Genet.* 124:783-789 (1990), all of which are herein incorporated by reference in their entirety).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction ("PCR") (Mullis, et al., *Cold Spring Harbor Symp. Quant. Biol.* 51:263-273 (1986); Erlich, et al., European Patent Appln. 50,424; European Patent Appln. 84,796, European Patent Application 258, 017, European Patent Appln. 237,362; Mullis, European Patent Appln. 201,184; Mullis, et al., U.S. Pat. No. 4,683,202; Erlich., U.S. Pat. No. 4,582,788; and Saiki, et al., U.S. Pat. No. 4,683,194, all of which are herein incorporated by reference), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci. (U.S.A.)* 88:189-193 (1991), the entirety of which is herein incorporated by reference). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069, the entirety of which is herein incorporated by reference).

The "Oligonucleotide Ligation Assay" ("OLA") may alternatively be employed (Landegren, et al., *Science* 241:1077-1080 (1988), the entirety of which is herein incorporated by reference). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, et al. have described a nucleic acid detection assay that combines attributes of PCR and OLA (Nickerson, et al., *Proc. Natl. Acad. Sci. (U.S.A.)* 87:8923-8927 (1990), the entirety of which is herein incorporated by reference). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu, et al., *Genomics* 4:560 (1989), the entirety of which is herein incorporated by reference), and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek, et al., U.S. Pat. No. 5,130,238; Davey, et al., European Patent Application 329,822; Schuster et al., U.S. Pat. No. 5,169,766; Miller, et al., PCT Application WO 89/06700; Kwoh, et al., *Proc. Natl. Acad. Sci.* (U.S.A.) 86:1173-1177 (1989); Gingeras, et al., PCT Application WO 88/10315; Walker, et al., *Proc. Natl. Acad. Sci. (U.S.A.)* 89:392-396 (1992), all of which are herein incorporated by reference in their entirety).

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and plant genetic analyses (Glassberg, UK Patent Application 2135774; Skolnick, et al., *Cytogen. Cell Genet.* 32:58-67 (1982); Botstein, et al., *Ann. J. Hum. Genet.* 32:314-331 (1980); Fischer, et al. (PCT Application WO90/13668); Uhlen, PCT Application WO90/11369).

Polymorphisms can also be identified by Single Strand Conformation Polymorphism (SSCP) analysis. The SSCP technique is a method capable of identifying most sequence variations in a single strand of DNA, typically between 150 and 250 nucleotides in length (Elles, *Methods in Molecular Medicine: Molecular Diagnosis of Genetic Diseases*, Humana Press (1996), the entirety of which is herein incorporated by reference); Orita et al., *Genomics* 5: 874-879 (1989), the entirety of which is herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to Lee et al., *Anal. Biochem.* 205: 289-293 (1992), the entirety of which is herein incorporated by reference; Suzuki et al., *Anal. Biochem.* 192: 82-84 (1991), the entirety of which is herein incorporated by reference; Lo et al., *Nucleic Acids Research* 20: 1005-1009 (1992), the entirety of which is herein incorporated by reference; Sarkar et al., *Genomics* 13: 441-443 (1992), the entirety of which is herein incorporated by reference). It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA. Vos, et al., *Nucleic Acids Res.* 23:4407-4414 (1995), the entirety of which is herein incorporated by reference. This method allows for the specific co-amplification of high numbers of restriction fragments, which can be visualized by PCR without knowledge of the nucleic acid sequence.

AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel.

AFLP analysis has been performed on *Salix* (Beismann, et al., *Mol. Ecol.* 6:989-993 (1997), the entirety of which is herein incorporated by reference); *Acinetobacter* (Janssen, et al., *Int. J. Syst. Bacteriol* 47:1179-1187 (1997), the entirety of which is herein incorporated by reference), *Aeromonas popoffi* (Huys, et al., *Int. J. Syst. Bacteriol.* 47:1165-1171 (1997), the entirety of which is herein incorporated by reference), rice (McCouch, et al., *Plant Mol. Biol.* 35:89-99 (1997), the entirety of which is herein incorporated by reference); Nandi, et al., *Mol. Gen. Genet.* 255:1-8 (1997); Cho, et al., *Genome* 39:373-378 (1996), herein incorporated by reference), barley (*Hordeum vulgare*) (Simons, et al., *Genomics* 44:61-70 (1997), the entirety of which is herein incorporated by reference; Waugh, et al., *Mol. Gen. Genet.* 255:311-321 (1997), the entirety of which is herein incorporated by reference; Qi, et al., *Mol. Gen. Genet.* 254:330-336 (1997), the entirety of which is herein incorporated by reference; Becker, et al., *Mol. Gen. Genet.* 249:65-73 (1995), the entirety of which is herein incorporated by reference), potato (Van der Voort, et al., *Mol. Gen. Genet.* 255:438-447 (1997), the entirety of which is herein incorporated by reference; Meksem, et al., *Mol. Gen. Genet.* 249:74-81 (1995), the entirety of which is herein incorporated by reference), *Phytophthora infestans* (Van der Lee, et al., *Fungal Genet. Biol.* 21:278-291 (1997), the entirety of which is herein incorporated by reference), *Bacillus anthracis* (Keim, et al., *J. Bacteriol.* 179:818-824 (1997)), *Astragalus cremnophylax* (Travis, et al., *Mol. Ecol.* 5:735-745 (1996), the entirety of which is herein incorporated by reference), *Arabidopsis* (Cnops, et al., *Mol. Gen. Genet.* 253:32-41 (1996), the entirety of which is herein incorporated by reference), *Escherichia coli* (Lin, et al., *Nucleic Acids Res.* 24:3649-3650 (1996), the entirety of which is herein incorporated by reference), *Aeromonas* (Huys, et al., *Int. J. Syst. Bacteriol.* 46:572-580 (1996), the entirety of which is herein incorporated by reference), nematode (Folkertsma, et al., *Mol. Plant. Microbe Interact.* 9:47-54 (1996), the entirety of which is herein incorporated by reference), tomato (Thomas, et al., *Plant J.* 8:785-794 (1995), the entirety of which is herein incorporated by reference), and human (Latorra, et al., *PCR Methods Appl.* 3:351-358 (1994)). AFLP analysis has also been used for fingerprinting mRNA (Money, et al., *Nucleic Acids Res.* 24:2616-2617 (1996), the entirety of which is herein incorporated by reference; Bachem, et al., *Plant J.* 9:745-753 (1996), the entirety of which is herein incorporated by reference). It is understood that one or more of the nucleic acids of the present invention, may be utilized as markers or probes to detect polymorphisms by AFLP analysis for fingerprinting mRNA.

Polymorphisms may also be found using random amplified polymorphic DNA (RAPD) (Williams et al., *Nucl. Acids Res.* 18: 6531-6535 (1990), the entirety of which is herein incorporated by reference) and cleaveable amplified polymorphic sequences (CAPS) (Lyamichev et al., *Science* 260: 778-783 (1993), the entirety of which is herein incorporated by reference). It is understood that one or more of the nucleic acids of the present invention, may be utilized as markers or probes to detect polymorphisms by RAPD or CAPS analysis.

Polymorphisms are useful, through linkage analysis, to define the genetic distances or physical distances between polymorphic traits. A physical map or ordered array of genomic DNA fragments in the desired region containing the gene may be used to characterize and isolate genes corresponding to desirable traits. For this purpose, yeast artificial chromosomes (YACs), bacterial artificial chromosomes (BACs), and cosmids are appropriate vectors for cloning large segments of DNA molecules. Although fewer clones are needed to make a contig for a specific genomic region by using YACs (Agyare et al., *Genome Res.* 7: 1-9 (1997), the entirety of which is herein incorporated by reference; James et al., *Genomics* 32: 425-430 (1996), the entirety of which is herein incorporated by reference), chimerism in the inserted DNA fragment can arise. Cosmids are convenient for handling smaller-size DNA molecules and may be used for transformation in developing transgenic plants. BACs also carry DNA fragments and are less prone to chimerism.

Through genetic mapping, a fine scale linkage map can be developed using DNA markers and, then, a genomic DNA library of large-sized fragments can be screened with molecular markers linked to the desired trait. Molecular markers are advantageous for agronomic traits that are otherwise difficult to tag, such as resistance to pathogens, insects and nematodes, tolerance to abiotic stress, quality parameters and quantitative traits such as high yield potential.

The essential requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) the entirety of which is herein incorporated by reference and further described by Aris and Moreno-González, *Plant Breeding*, Hayward et al., (eds.) Chapman & Hall, London, pp. 314-331 (1993), the entirety of which is herein incorporated by reference.

Additional models can be used. Many modifications and alternative approaches to interval mapping have been reported, including the use of non-parametric methods (Kruglyak and Lander, *Genetics* 139:1421-1428 (1995), the entirety of which is herein incorporated by reference). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994), both of which are herein incorporated by reference in their entirety). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), the entirety of which is herein incorporated by reference and Zeng, *Genetics* 136:1457-1468 (1994) the entirety of which is herein incorporated by reference. Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), the entirety of which is herein incorporated by reference, thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995), the entirety of which is herein incorporated by reference).

Selection of an appropriate mapping population is important to map construction. The choice of an appropriate mapping population depends on the type of marker systems employed (Tanksley et al., *Molecular mapping plant chromosomes. Chromosome structure and function: Impact of new concepts*, Gustafson and Appels (eds.), Plenum Press, New York, pp 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, *Measurement of Linkage in Heredity*, Methuen and Co., (1938), the entirety of which is herein incorporated by reference). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (*U.S.A.*) 89:1477-1481 (1992), the entirety of which is herein incorporated by reference). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., *Proc. Natl. Acad. Sci.* (*U.S.A.*) 88:9828-9832 (1991), the entirety of which is herein incorporated by reference). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

It is understood that one or more of the nucleic acid molecules of the present invention may be used as molecular markers. It is also understood that one or more of the protein molecules of the present invention may be used as molecular markers.

In accordance with this aspect of the present invention, a sample nucleic acid is obtained from plants cells or tissues. Any source of nucleic acid may be used. Preferably, the nucleic acid is genomic DNA. The nucleic acid is subjected to restriction endonuclease digestion. For example, one or more EST nucleic acid molecule or fragment thereof can be used as a probe in accordance with the above-described polymorphic methods. The polymorphism obtained in this approach can then be cloned to identify the mutation at the coding region which alters the protein's structure or regulatory region of the gene which affects its expression level.

In one aspect of the present invention, an evaluation can be conducted to determine whether a particular mRNA molecule is present. One or more of the nucleic acid molecules of the present invention, preferably one or more of the EST nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A principle of in situ hybridization is that a labeled, single-stranded nucleic acid probe will hybridize to a complementary strand of cellular DNA or RNA and, under the appropriate conditions, these molecules will form a stable hybrid. When nucleic acid hybridization is combined with histological techniques, specific DNA or RNA sequences can be identified within a single cell. An advantage of in situ hybridization over more conventional techniques for the detection of nucleic acids is that it allows an investigator to determine the precise spatial population (Angerer et al., *Dev. Biol.* 101: 477-484 (1984), the entirety of which is herein incorporated by reference; Angerer et al., *Dev. Biol.* 112: 157-166 (1985), the entirety of which is herein incorporated by reference; Dixon et al., *EMBO J.* 10: 1317-1324 (1991), the entirety of which is herein incorporated by reference). In situ hybridization may be used to measure the steady-state level of RNA accumulation. It is a sensitive technique and RNA sequences present in as few as 5-10 copies per cell can be detected (Hardin et al., *J. Mol. Biol.* 202: 417-431. (1989), the entirety of which is herein incorporated by reference). A number of protocols have been devised for in situ hybridization, each with tissue preparation, hybridization, and washing conditions (Meyerowitz, *Plant Mol. Biol. Rep.* 5: 242-250 (1987), the entirety of which is herein incorporated by reference; Cox and Goldberg, In: *Plant Molecular Biology: A Practical Approach* (ed. C. H. Shaw), pp. 1-35. IRL Press, Oxford (1988), the entirety of which is herein incorporated by reference; Raikhel et al., *In situ RNA hybridization in plant tissues. In Plant Molecular Biology Manual*, vol. B9: 1-32. Kluwer Academic Publisher, Dordrecht, Belgium (1989), the entirety of which is herein incorporated by reference).

In situ hybridization also allows for the localization of proteins within a tissue or cell (Wilkinson, *In Situ Hybridization*, Oxford University Press, Oxford (1992), the entirety of which is herein incorporated by reference; Langdale, *In Situ Hybridization* 165-179 In: *The Maize Handbook*, eds. Freeling and Walbot, Springer-Verlag, New York (1994), the entirety of which is herein incorporated by reference). It is understood that one or more of the molecules of the present invention, preferably one or more of the EST nucleic acid molecules of the present invention or one or more of the antibodies of the present invention may be utilized to detect the level or pattern of a protein or fragment thereof by in situ hybridization.

Fluorescent in situ hybridization also enables the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 17: 101-109 (1991), the entirety of which is herein incorporated by reference; Gustafson et al., *Proc. Nat'l. Acad. Sci.* (*U.S.A*). 87: 1899-1902 (1990), herein incorporated by reference; Mukai and Gill, *Genome* 34: 448-452. (1991); Schwarzacher and Heslop-Harrison, *Genome* 34: 317-323 (1991); Wang et al., *Jpn. J. Genet.* 66: 313-316 (1991), the entirety of which is herein incorporated by reference; Parra and Windle, *Nature*

Genetics, 5: 17-21 (1993), the entirety of which is herein incorporated by reference). It is understood that the nucleic acid molecules of the present invention may be used as probes or markers to localize sequences along a chromosome.

It is also understood that one or more of the molecules of the present invention, preferably one or more of the EST nucleic acid molecules of the present invention or one or more of the antibodies of the present invention may be utilized to detect the expression level or pattern of a protein or mRNA thereof by in situ hybridization.

Another method to localize the expression of a molecule is tissue printing. Tissue printing provides a way to screen, at the same time on the same membrane many tissue sections from different plants or different developmental stages. Tissue-printing procedures utilize films designed to immobilize proteins and nucleic acids. In essence, a freshly cut section of an organ is pressed gently onto nitrocellulose paper, nylon membrane or polyvinylidene difluoride membrane. Such membranes are commercially available (e.g. Millipore, Bedford, Mass.). The contents of the cut cell transfer onto the membrane, and the molecules are immobilized to the membrane. The immobilized molecules form a latent print that can be visualized with appropriate probes. When a plant tissue print is made on nitrocellulose paper, the cell walls leave a physical print that makes the anatomy visible without further treatment (Varner and Taylor, *Plant Physiol.* 91: 31-33 (1989), the entirety of which is herein incorporated by reference).

Tissue printing on substrate films is described by Daoust, *Exp. Cell Res.* 12: 203-211 (1957), the entirety of which is herein incorporated by reference, who detected amylase, protease, ribonuclease, and deoxyribonuclease in animal tissues using starch, gelatin, and agar films. These techniques can be applied to plant tissues (Yomo and Taylor, *Planta* 112:35-43 (1973); Harris and Chrispeels, *Plant Physiol.* 56: 292-299 (1975). Advances in membrane technology have increased the range of applications of Daoust's tissue-printing techniques allowing (Cassab and Varner, *J. Cell. Biol.* 105: 2581-2588 (1987), the entirety of which is herein incorporated by reference; the histochemical localization of various plant enzymes and deoxyribonuclease on nitrocellulose paper and nylon (Spruce et al., *Phytochemistry*, 26: 2901-2903 (1987), the entirety of which is herein incorporated by reference; Barres et al. *Neuron* 5: 527-544 (1990), the entirety of which is herein incorporated by reference; the entirety of which is herein incorporated by reference; Reid and Pont-Lezica, *Tissue Printing: Tools for the Study of Anatomy, Histochemistry, and Gene Expression*, Academic Press, New York, N.Y. (1992), the entirety of which is herein incorporated by reference; Reid et al. *Plant Physiol.* 93: 160-165 (1990), herein incorporate by reference; Ye et al. *Plant J.* 1: 175-183 (1991), the entirety of which is herein incorporated by reference).

It is understood that one or more of the molecules of the present invention, preferably one or more of the EST nucleic acid molecules of the present invention or one or more of the antibodies of the present invention may be utilized to detect the presence or quantity of a protein by tissue printing.

Further, it is also understood that any of the nucleic acid molecules of the present invention may be used as marker nucleic acids and or probes in connection with methods that require probes or marker nucleic acids. As used herein, a probe is an agent that is utilized to determine an attribute or feature (e.g. presence or absence, location, correlation, etc.) or a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

A microarray-based method for high-throughput monitoring of gene expression may be utilized to measure expression response Schena et al., *Science* 270:467-470 (1995); http://cmgm.stanford.edu/pbrown/array.html; Shalon, Ph.D. Thesis, Stanford University (1996). This approach is based on using arrays of DNA targets (e.g. cDNA inserts, colonies, or polymerase chain reaction products) for hybridization to a "complex probe" prepared with RNA extracted from a given cell line or tissue. The probe may be produced by reverse transcription of mRNA or total RNA and labeled with radioactive or fluorescent labeling. The probe is complex in that it contains many different sequences in various amounts, corresponding to the numbers of copies of the original mRNA species extracted from the sample.

The initial RNA source will typically be derived from a physiological source. The physiological source may be derived from a variety of eukaryotic sources, with physiological sources of interest including sources derived from single celled organisms such as yeast and multicellular organisms, including plants and animals, particularly plants, where the physiological sources from multicellular organisms may be derived from particular organs or tissues of the multicellular organism, or from isolated cells derived therefrom. The physiological sources may be derived from multicellular organisms at different developmental stages (e.g., 10-day-old seedlings), grown under different environmental conditions (e.g., drought-stressed plants) or treated with chemicals.

In obtaining the sample of RNAs to be analyzed from the physiological source from which it is derived, the physiological source may be subjected to a number of different processing steps, where such processing steps might include tissue homogenation, cell isolation and cytoplasmic extraction, nucleic acid extraction and the like, where such processing steps are known to the those of skill in the art. Methods of isolating RNA from cells, tissues, organs or whole organisms are known to those of skill in the art and are described in Maniatis et al., *Molecular Cloning: A Laboratory Manual* (Cold Spring Harbor Press) (1989).

The DNA may be placed on nylon or glass "microarrays" regularly arranged with a spot spacing of 1 mm or less. Expression levels can be measured for hundreds or thousands of genes, by using less than 2 micrograms of polyA+RNA and determining the relative mRNA abundances down to one in ten thousand or less (Granjeaud et. al., *BioEssays* 21:781-790 (1999)).

In addition to arrays of cDNA clones or inserts, arrays of oligonucleotides are also used to study differential gene expression. In an oligonucleotide array, the genes of interest are represented by a series of approximately 20 nucleotide oligomers that are unique to each gene. Labeled mRNA is prepared and hybridization signals are detected from specific sets of oligos that represent different genes supplemented by a set of control oligonucleotides. Potential advantages of the oligonucleotide array include enhanced specificity and sensitivity through the parallel analysis of "perfect match" oligos and "mismatch" oligos for each gene. The hybridization conditions can be adjusted to distinguish a perfect heteroduplex from a single base mismatch, thus allowing subtraction of nonspecific hybridization signals from specific hybridization signals. A disadvantage of oligonucleotide arrays relative to cDNA arrays is the limitation of the technology to genes of known sequence (Granjeaud et. al., *BioEssays* 21:781-790 (1991); Carulli et al., *Journal of Cellular Biochemistry Supplements* 30/31:286-296 (1998)).

These techniques have been successfully used to characterize patterns of gene expression associated with, for example, various important physiological changes in yeast, including the mitotic cell cycle, the heat shock response, and comparison between mating types. Once a set of comparable expression profiles is obtained, e.g. for cells at different time points or at different cellular states, a clustering algorithm generally is used to group sets of genes which share similar expression patterns. The clusters obtained can then be analyzed in the light of available functional annotations, often leading to associations of poorly characterized genes with genes whose function and regulation are better understood.

Regulatory networks that control gene expression can be characterized using microarray technology (DeRisi et al., *Science* 278: 680-686 (1997); Winzler et al. *Science* 28: 1194-1197 (1998); Cho et al. *Mol Cell* 2: 65-73 (1998); Spellman et al. *Mol Biol Cell* 95: 14863-14868 (1998). For example, it is has been reported that both cDNA and oligonucleotide arrays have been used to monitor gene expression in synchronized cell cultures. Analysis of the corresponding temporal patterns of gene expression resulted in the identification of over 400 cell cycle-regulated genes. In order to identify possible common regulatory mechanisms accounting for co-expression, consensus motifs in putative regulatory sequences upstream of the corresponding ORFs were examined. This resulted in the identification of several new potential binding sites for known factors or complexes involved in the coordinated transcription of genes during specific phases of the cell cycle (Thieffry, D. *BioEssays* 21: 895-899 (1999)).

The microarray approach may be used with polypeptide targets (U.S. Pat. Nos. 5,445,934; 5,143,854; 5,079,600; 4,923,901) synthesized on a substrate (microarray) and these polypeptides can be screened with either (Fodor et al., *Science* 251:767-773 (1991)).

As disclosed in U.S. Pat. No. 5,445,934 arrays with nucleic acid molecules can comprise a substrate with a surface comprising $10^3$ or more groups of oligonucleotides with different, known sequences covalently attached to the surface in discrete known regions, e.g. $10^4$ or $10^5$ or $10^6$ or more different groups of known sequences in discrete known regions. In preferred arrays $10^3$ or more groups of oligonucleotides occupy a total area of less than 1 $cm^2$. In preferred embodiments the groups of oligonucleotides are at least 50% pure within the discrete known regions."

It is understood that one or more of the nucleic acid molecules or protein or fragments thereof of the invention may be utilized in a microarray-based method.

In a preferred embodiment of the present invention microarrays may be prepared that comprise nucleic acid molecules where preferably at least 10%, preferably at least 25%, more preferably at least 50% and even more preferably at least 75%, 80%, 85%, 90% or 95% of the nucleic acid molecules located on that array are selected from the group of nucleic acid molecules that specifically hybridize to one or more nucleic acid molecule having a nucleic acid sequence selected from the group of SEQ ID NO: 1 through SEQ ID NO: 17472 or complement thereof or fragments of either.

A particular preferred microarray embodiment of the present invention is a microarray comprising nucleic acid molecules encoding genes or fragments thereof that are homologues of known genes or nucleic acid molecules that comprise genes or fragment thereof that elicit only limited or no matches to known genes. A further preferred microarray embodiment of the present invention is a microarray comprising nucleic acid molecules having genes or fragments thereof that are homologues of known genes and nucleic acid molecules that comprise genes or fragment thereof that elicit only limited or no matches to known genes. Site-directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site-directed mutagenesis are often employed. These are cassette mutagenesis (Wells et al., *Gene* 34:315-23 (1985), the entirety of which is herein incorporated by reference), primer extension (Gilliam et al., *Gene* 12:129-137 (1980), the entirety of which is herein incorporated by reference); Zoller and Smith, *Methods Enzymol.* 100:468-500 (1983), the entirety of which is herein incorporated by reference; and Dalbadie-McFarland et al., *Proc. Natl. Acad. Sci.* (*U.S.A.*) 79:6409-6413 (1982), the entirety of which is herein incorporated by reference) and methods based upon PCR (Scharf et al., *Science* 233:1076-1078 (1986), the entirety of which is herein incorporated by reference; Higuchi et al., *Nucleic Acids Res.* 16:7351-7367 (1988), the entirety of which is herein incorporated by reference). Site-directed mutagenesis approaches are also described in European Patent 0 385 962, the entirety of which is herein incorporated by reference, European Patent 0 359 472, the entirety of which is herein incorporated by reference, and PCT Patent Application WO 93/07278, the entirety of which is herein incorporated by reference.

Site-directed mutagenesis strategies have been applied to plants for both in vitro as well as in vivo site-directed mutagenesis (Lanz et al., *J. Biol. Chem.* 266:9971-6 (1991), the entirety of which is herein incorporated by reference; Kovgan and Zhdanov, *Biotekhnologiya* 5:148-154; No. 207160n, Chemical Abstracts 110:225 (1989), the entirety of which is herein incorporated by reference; Ge et al., *Proc. Natl. Acad. Sci.* (*U.S.A.*) 86:4037-4041 (1989), the entirety of which is herein incorporated by reference, Zhu et al., *J. Biol. Chem.* 271:18494-18498 (1996), Chu et al., *Biochemistry* 33:6150-6157 (1994), the entirety of which is herein incorporated by reference, Small et al., *EMBO J.* 11:1291-1296 (1992), the entirety of which is herein incorporated by reference, Cho et al., *Mol. Biotechnol.* 8:13-16 (1997), Kita et al., *J. Biol. Chem.* 271:26529-26535 (1996), the entirety of which is herein incorporated by reference, Jin et al., *Mol. Microbiol.* 7:555-562 (1993), the entirety of which is herein incorporated by reference, Hatfield and Vierstra, *J. Biol. Chem.* 267:14799-14803 (1992), the entirety of which is herein incorporated by reference, Zhao et al., *Biochemistry* 31:5093-5099 (1992), the entirety of which is herein incorporated by reference).

Any of the nucleic acid molecules of the present invention may either be modified by site-directed mutagenesis or used as, for example, nucleic acid molecules that are used to target other nucleic acid molecules for modification. It is understood that mutants with more than one altered nucleotide can be constructed using techniques that practitioners skilled in the art are familiar with such as isolating restriction fragments and ligating such fragments into an expression vector (see, for example, Sambrook et al., *Molecular Cloning: A Laboratory Manual*, Cold Spring Harbor Press (1989)).

Sequence-specific DNA-binding proteins play a role in the regulation of transcription. The isolation of recombinant cDNAs encoding these proteins facilitates the biochemical analysis of their structural and functional properties. Genes encoding such DNA-binding proteins have been isolated using classical genetics (Vollbrecht et al., *Nature* 350: 241-243 (1991), the entirety of which is herein incorporated by reference) and molecular biochemical approaches, including the screening of recombinant cDNA libraries with antibodies (Landschulz et al., *Genes Dev.* 2: 786-800 (1988), the entirety of which is herein incorporated by reference) or DNA probes (Bodner et al., *Cell* 55: 505-518 (1988), the entirety of which is herein incorporated by reference). In addition, an in situ screening procedure has been used and has facilitated the isolation of sequence-specific DNA-binding proteins from various plant species (Gilmartin et al., *Plant Cell* 4: 839-849 (1992), the entirety of which is herein incorporated by reference; Schindler et al., *EMBO J.* 11: 1261-1273 (1992) the entirety of which is herein incorporated by reference). An in situ screening protocol does not require the purification of the protein of interest (Vinson et al., *Genes Dev.* 2: 801-806 (1988), the entirety of which is herein incorporated by reference; Singh et al., *Cell* 52: 415-423 (1988), the entirety of which is herein incorporated by reference).

Steps may be employed to characterize DNA-protein interactions. The first is to identify promoter fragments that interact with DNA-binding proteins, to titrate binding activity, to determine the specificity of binding, and to determine whether a given DNA-binding activity can interact with related DNA sequences (Sambrook et al., *Molecular Cloning: A Laboratory Manual*, $2^{nd}$ edition. Cold Spring Harbor Laboratory Press, Cold Spring Harbor, N.Y. (1989). Electrophoretic mobility-shift assay is a widely used assay. The assay provides a simple, rapid, and sensitive method for detecting DNA-binding proteins based on the observation that the mobility of a DNA fragment through a nondenaturing, low-ionic strength polyacrylamide gel is retarded upon association with a DNA-binding protein (Fried and Crother, *Nucleic Acids Res.* 9: 6505-6525 (1981), the entirety of which is herein incorporated by reference). When one or more specific binding activities have been identified, the exact sequence of the DNA bound by the protein may be determined. Several procedures for characterizing protein/DNA-binding sites are used, including methylation and ethylation interference assays (Maxam and Gilbert, *Methods Enzymol.* 65: 499-560 (1980), the entirety of which is herein incorporated by reference; Wissman and Hillen, *Methods Enzymol.* 208: 365-379 (1991), the entirety of which is herein incorporated by reference) and footprinting techniques employing DNase I (Galas and Schmitz, *Nucleic Acids Res.* 5: 3157-3170 (1978), the entirety of which is herein incorporated by reference), 1,10-phenanthroline-copper ion methods (Sigman et al., *Methods Enzymol.* 208: 365-379 (1991), the entirety of which is herein incorporated by reference) or hydroxyl radical methods (Dixon et al., *Methods Enzymol.* 208: 380-413 (1991), the entirety of which is herein incorporated by reference). It is understood that one or more of the nucleic acid molecules of the present invention, preferably one or more of the EST nucleic acid molecules of the present invention may be utilized to identify a protein or fragment thereof that specifically binds to a nucleic acid molecule of the present invention. It is also understood that one or more of the protein molecules or fragments thereof of the present invention may be utilized to identify a nucleic acid molecule that specifically binds to it.

The two-hybrid system is based on the fact that many cellular functions are carried out by proteins that interact (physically) with one another. Two-hybrid systems have been used to probe the function of new proteins (Chien et al., *Proc. Natl. Acad. Sci. (U.S.A.)* 88: 9578-9582 (1991) the entirety of which is herein incorporated by reference; Durfee et al., *Genes Dev.* 7: 555-569 (1993) the entirety of which is herein incorporated by reference; Choi et al., *Cell* 78: 499-512 (1994), the entirety of which is herein incorporated by reference; Kranz et al., *Genes Dev.* 8: 313-327 (1994), the entirety of which is herein incorporated by reference).

Interaction mating techniques have facilitated a number of two-hybrid studies of protein-protein interaction. Interaction mating has been used to examine interactions between small sets of tens of proteins (Finley and Brent, *Proc. Natl. Acad. Sci. (U.S.A.)* 91: 12098-12984 (1994), the entirety of which is herein incorporated by reference), larger sets of hundreds of proteins, (Bendixen et al., *Nucl. Acids Res.* 22: 1778-1779 (1994), the entirety of which is herein incorporated by reference) and to comprehensively map proteins encoded by a small genome (Bartel et al., *Nature Genetics* 12: 72-77 (1996), the entirety of which is herein incorporated by reference). This technique utilizes proteins fused to the DNA-binding domain and proteins fused to the activation domain. They are expressed in two different haploid yeast strains of opposite mating type, and the strains are mated to determine if the two proteins interact. Mating occurs when haploid yeast strains come into contact and result in the fusion of the two haploids into a diploid yeast strain. An interaction can be determined by the activation of a two-hybrid reporter gene in the diploid strain. The primary advantage of this technique is that it reduces the number of yeast transformations needed to test individual interactions. It is understood that the protein-protein interactions of protein or fragments thereof of the present invention may be investigated using the two-hybrid system and that any of the nucleic acid molecules of the present invention that encode such proteins or fragments thereof may be used to transform yeast in the two-hybrid system.

*Synechocystis* 6803 is a photosynthetic Cyanobacterium capable of oxygenic photosynthesis as well as heterotrophic growth in the absence of light. The entire genome has been sequenced, and it is reported to have a circular genome size of 3.57 Mbp containing 3168 potential open reading frames. Open reading frames (ORFs) were identified based upon their homology to other reported ORFs and by using ORF identification computer programs. Sixteen hundred potential ORFs were assigned based on their homology to previously identified ORFs. Of these 1600 ORFs, 145 were identical to reported ORFs (Kaneko et al., *DNA Research* 3:109-36 (1996), herein incorporated by reference in its entirety).

Several prokaryote promoters have been used in *Synechocystis* to express heterologous genes including the tac, lac, and lambda phage promoters (Bryant (ed.), *The Molecular Biology of Cyanobacteria*, Kluwer Academic Publishers, (1994); Ferino and Chauvat, *Gene* 84:257-266 (1989), both of which are herein incorporated by reference in their entirety). Several bacterial origins of replication such as RSF1010 and ACYC are reported to replicate in *Synechocystis* (Mermet-Bouvier and Chauvat, *Current Microbiology* 28:145-148 (1994); Kuhlemeier et al., *Mol. Gen. Genet.* 184:249-254 (1981), both of which are herein incorporated by reference in their entirety).

*Synechocystis* has been used to study gene regulation by gene replacement through homologous recombination or by gene disruption using antibiotic resistance markers (Pakrasi et al., *EMBO* 7:325-332 (1988), herein incorporated by reference in its entirety). In such gene regulation studies, double reciprocal homologous regions of the host genome flanking the gene of interest recombine to stably integrate the gene of interest into the genome. The gene of interest can be expressed once that gene has been stably integrated into the genome. Biochemical analysis can be performed to study the effect of the replaced or deleted gene.

It is understood that the agents of the present invention may be employed in a *Synechocystis* system.

Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. Such genetic material may be transferred into either monocotyledons and dicotyledons including but not limited to the crops, maize and soybean (See specifically, Chistou, *Particle Bombardment for Genetic Engineering of Plants*, pp 63-69 (maize), pp 50-60 (soybean), Biotechnology Intelligence Unit. Academic Press, San Diego, Calif. (1996), the entirety of which is herein incorporated by reference and generally Chistou, *Particle Bombardment for Genetic Engineering of Plants*, Biotechnology Intelligence Unit. Academic Press, San Diego, Calif. (1996), the entirety of which is herein incorporated by reference).

Transfer of a nucleic acid that encodes for a protein can result in overexpression of that protein in a transformed cell or transgenic plant. One or more of the proteins or fragments thereof encoded by nucleic acid molecules of the present invention may be overexpressed in a transformed cell or transformed plant. Such overexpression may be the result of transient or stable transfer of the exogenous material.

Exogenous genetic material may be transferred into a plant cell by the use of a DNA vector or construct designed for such a purpose. Design of such a vector is generally within the skill of the art (See, Plant Molecular Biology: A Laboratory Manual eds. Clark, Springer, New York (1997), the entirety of which is herein incorporated by reference).

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci. (U.S.A.)* 84:5745-5749 (1987), the entirety of which is herein incorporated by reference), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), the entirety of which is herein incorporated by reference) and the CAMV 35S promoter (Odell et al., *Nature* 313:810-812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628 (1987), the entirety of which is herein incorporated by reference), the sucrose synthase promoter (Yang et al., *Proc. Natl. Acad. Sci. (U.S.A.)* 87:4144-4148 (1990), the entirety of which is herein incorporated by reference), the R gene complex promoter (Chandler et al., *The Plant Cell* 1:1175-1183 (1989), the entirety of which is herein incorporated by reference), and the chlorophyll a/b binding protein gene promoter, etc. These promoters have been used to create DNA constructs which have been expressed in plants; see, e.g., PCT publication WO 84/02913, herein incorporated by reference in its entirety.

Promoters which are known or are found to cause transcription of DNA in plant cells can be used in the present invention. Such promoters may be obtained from a variety of sources such as plants and plant viruses. It is preferred that the particular promoter selected should be capable of causing sufficient expression to result in the production of an effective amount of a protein to cause the desired phenotype. In addition to promoters which are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci. (U.S.A.)* 87:3459-3463 (1990), herein incorporated by reference in its entirety), the chloroplast fructose-1,6-biphosphatase (FBPase) promoter from wheat (Lloyd et al., *Mol. Gen. Genet.* 225:209-216 (1991), herein incorporated by reference in its entirety), the nuclear photosynthetic ST-LS1 promoter from potato (Stockhaus et al., *EMBO J.* 8:2445-2451 (1989), herein incorporated by reference in its entirety), the phenylalanine ammonia-lyase (PAL) promoter and the chalcone synthase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994), herein incorporated by reference in its entirety), the promoter for the Cab-1 gene from wheat (Fejes et al., *Plant Mol. Biol.* 15:921-932 (1990), herein incorporated by reference in its entirety), the promoter for the CAB-1 gene from spinach (Lubberstedt et al., *Plant Physiol.* 104:997-1006 (1994), herein incorporated by reference in its entirety), the promoter for the cab1R gene from rice (Luan et al., *Plant Cell.* 4:971-981 (1992), the entirety of which is herein incorporated by reference), the pyruvate, orthophosphate dikinase (PPDK) promoter from maize (Matsuoka et al., *Proc. Natl. Acad. Sci. (U.S.A.)* 90: 9586-9590 (1993), herein incorporated by reference in its entirety), the promoter for the tobacco Lhcb1*2 gene (Cerdan et al., *Plant Mol. Biol.* 33: 245-255. (1997), herein incorporated by reference in its entirety), the *Arabidopsis thaliana* SUC2 sucrose-H+ symporter promoter (Truernit et al., *Planta.* 196: 564-570 (1995), herein incorporated by reference in its entirety), and the promoter for the thylacoid membrane proteins from spinach (psaD, psaF, psaE, PC, FNR, atpC, atpD, cab, rbcS). Other promoters for the chlorophyl a/b-binding proteins may also be utilized in the present invention, such as the promoters for LhcB gene and PsbP gene from white mustard (*Sinapis alba*; Kretsch et al., *Plant Mol. Biol.* 28: 219-229 (1995), the entirety of which is herein incorporated by reference).

For the purpose of expression in sink tissues of the plant, such as the tuber of the potato plant, the fruit of tomato, or the seed of maize, wheat, rice, and barley, it is preferred that the promoters utilized in the present invention have relatively high expression in these specific tissues. A number of promoters for genes with tuber-specific or -enhanced expression are known, including the class I patatin promoter (Bevan et al., *EMBO J.* 8: 1899-1906 (1986); Jefferson et al., *Plant Mol. Biol.* 14: 995-1006 (1990), both of which are herein incorporated by reference in their entirety), the promoter for the potato tuber ADPGPP genes, both the large and small subunits, the sucrose synthase promoter (Salanoubat and Belliard, *Gene.* 60: 47-56 (1987), Salanoubat and Belliard, *Gene.* 84: 181-185 (1989), both of which are incorporated by reference in their entirety), the promoter for the major tuber proteins including the 22 kd protein complexes and proteinase inhibitors (Hannapel, *Plant Physiol.* 101: 703-704 (1993), herein incorporated by reference in its entirety), the promoter for the granule bound starch synthase gene (GBSS) (Visser et al., *Plant Mol. Biol.* 17: 691-699 (1991), herein incorporated by reference in its entirety), and other class I and II patatins promoters (Koster-Topfer et al., *Mol Gen Genet.* 219: 390-396 (1989); Mignery et al., *Gene.* 62: 27-44 (1988), both of which are herein incorporated by reference in their entirety).

Other promoters can also be used to express a fructose 1,6 bisphosphate aldolase gene in specific tissues, such as seeds or fruits. The promoter for β-conglycinin (Chen et al., *Dev. Genet.* 10: 112-122 (1989), herein incorporated by reference in its entirety) or other seed-specific promoters such as the napin and phaseolin promoters, can be used. The zeins are a group of storage proteins found in maize endosperm. Genomic clones for zein genes have been isolated (Pedersen et al., *Cell* 29: 1015-1026 (1982), herein incorporated by reference in its entirety), and the promoters from these clones, including the 15 kD, 16 kD, 19 kD, 22 kD, 27 kD, and gamma genes, could also be used. Other promoters known to function, for example, in maize, include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., *Mol. Cell. Biol.* 13: 5829-5842 (1993), herein incorporated by reference in its entirety). Examples of promoters suitable for expression in wheat include those promoters for the ADPglucose pyrophosphorylase (ADPGPP) subunits, the granule bound and other starch synthases, the branching and debranching enzymes, the embryogenesis-abundant proteins, the gliadins, and the glutenins. Examples of such promoters in rice include those promoters for the ADPGPP subunits, the granule bound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleurone specific proteins.

Root specific promoters may also be used. An example of such a promoter is the promoter for the acid chitinase gene (Samac et al., *Plant Mol. Biol.* 25: 587-596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci. (U.S.A.)* 86:7890-7894 (1989), herein incorporated by reference in its entirety). Other root cell specific promoters include those reported by Conkling et al. (Conkling et al., *Plant Physiol.* 93:1203-1211 (1990), the entirety of which is herein incorporated by reference).

Additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., *The Plant Cell* 1:977-984 (1989), the entirety of which is herein incorporated by reference).

Constructs or vectors may also include, with the coding region of interest, a nucleic acid sequence that acts, in whole or in part, to terminate transcription of that region. For example, such sequences have been isolated including the Tr7 3' sequence and the nos 3' sequence (Ingelbrecht et al., *The Plant Cell* 1:671-680 (1989), the entirety of which is herein incorporated by reference; Bevan et al., *Nucleic Acids Res.* 11:369-385 (1983), the entirety of which is herein incorporated by reference), or the like.

A vector or construct may also include regulatory elements. Examples of such include the Adh intron 1 (Callis et al., *Genes and Develop.* 1:1183-1200 (1987), the entirety of which is herein incorporated by reference), the sucrose synthase intron (Vasil et al., *Plant Physiol.* 91:1575-1579 (1989), the entirety of which is herein incorporated by reference) and the TMV omega element (Gallie et al., *The Plant Cell* 1:301-311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985), the entirety of which is herein incorporated by reference) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988), the entirety of which is herein incorporated by reference) which encodes glyphosate resistance; a nitrilase gene which confers resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500-12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996), the entirety of which is herein incorporated by reference.

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5: 387-405 (1987), the entirety of which is herein incorporated by reference; Jefferson et al., *EMBO J.* 6: 3901-3907 (1987), the entirety of which is herein incorporated by reference); an R-locus gene, which encodes a product that regulates the production of anthocyanin pigments (red color) in plant tissues ((Dellaporta et al., Stadler Symposium 11:263-282 (1988), the entirety of which is herein incorporated by reference); a β-lactamase gene (Sutcliffe et al., *Proc. Natl. Acad. Sci. (U.S.A.)* 75: 3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234: 856-859 (1986), the entirety of which is herein incorporated by reference) a xylE gene (Zukowsky et al., *Proc. Natl. Acad. Sci. (U.S.A.)* 80:1101-1105 (1983), the entirety of which is herein incorporated by reference) which encodes a catechol diozygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a scriptable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Methods and compositions for transforming a bacteria and other microorganisms are known in the art (see for example Sambrook et al., *Molecular Cloning: A Laboratory Manual*, Second Edition, Cold Spring Harbor Laboratory Press, Cold Spring Harbor, N.Y., (1989), the entirety of which is herein incorporated by reference).

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc. (Pottykus, *Ann. Rev. Plant Physiol. Plant Mol. Biol.* 42:205-225 (1991), the entirety of which is herein incorporated by reference; Vasil, *Plant Mol. Biol.* 25: 925-937 (1994), the entirety of which is herein incorporated by reference. For example, electroporation has been used to transform maize protoplasts (Fromm et al., *Nature* 312:791-793 (1986), the entirety of which is herein incorporated by reference).

Other vector systems suitable for introducing transforming DNA into a host plant cell includes but is not limited to binary artificial chromosome (BIBAC) vectors (Hamilton et al., *Gene* 200:107-116, (1997), the entirety of which is herein incorporated by reference, and transfection with RNA viral vectors (Della-Cioppa et al., *Ann. N.Y. Acad. Sci.* (1996), 792 (Engineering Plants for Commercial Products and Applications), 57-61, the entirety of which is herein incorporated by reference.

Technology for introduction of DNA into cells is well known to those of skill in the art. Four general methods for delivering a gene into cells have been described: (1) chemical methods (Graham and van der Eb, *Virology*, 54:536-539 (1973), the entirety of which is herein incorporated by reference); (2) physical methods such as microinjection (Capecchi, *Cell* 22:479-488 (1980), electroporation (Wong and Neumann, *Biochem. Biophys. Res. Commun.*, 107:584-587 (1982); Fromm et al., *Proc. Natl. Acad. Sci. USA*, 82:5824-5828 (1985); U.S. Pat. No. 5,384,253; and the gene gun (Johnston and Tang, *Methods Cell Biol.* 43:353-365 (1994), all of which the entirety is herein incorporated by reference; (3) viral vectors (Clapp, *Clin. Perinatol.*, 20:155-168 (1993); Lu et al., *J. Exp. Med.*, 178:2089-2096 (1993); Eglitis and Anderson, *Biotechniques*, 6:608-614 (1988), all of which the entirety is herein incorporated by reference); and (4) receptor-mediated mechanisms (Curiel et al., *Hum. Gen. Ther.*, 3:147-154 (1992); Wagner et al., *Proc. Natl. Acad. Sci. USA*, 89:6099-6103 (1992), all of which the entirety is herein incorporated by reference).

Acceleration methods that may be used include, for example, microprojectile bombardment and the like. One example of a method for delivering transforming nucleic acid molecules to plant cells is microprojectile bombardment. This method has been reviewed by Yang and Christou, eds., *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum, and the like.

A particular advantage of microprojectile bombardment, in addition to it being an effective means of reproducibly, and stably transforming monocotyledons, is that neither the isolation of protoplasts (Cristou et al., *Plant Physiol.* 87:671-674 (1988), the entirety of which is herein incorporated by reference) nor the susceptibility of *Agrobacterium* infection is required. An illustrative embodiment of a method for delivering DNA into maize cells by acceleration is a biolistics g-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2: 603-618 (1990), the entirety of which is herein incorporated by reference). The screen disperses the tungsten nucleic acid particles so that they are not delivered to the recipient cells in large aggregates. A particle delivery system suitable for use with the present invention is the helium acceleration PDS-1000/He gun which is available from Bio-Rad Laboratories (Bio-Rad, Hercules, Calif.) (Sanford et al., *Technique* 3:3-16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos. In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)* 87:8526-8530 (1990); Svab and Maliga, *Proc. Natl. Acad. Sci. (U.S.A.)* 90:913-917 (1993); Staub and Maliga, *EMBO J.* 12:601-606 (1993); U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described (Fraley et al., *Biotechnology* 3:629-635 (1985); Rogers et al., *Meth. In Enzymol,* 153:253-277 (1987), both of which are herein incorporated by reference in their entirety. Further, the integration of the Ti-DNA is a relatively precise process resulting in few rearrangements. The region of DNA to be transferred is defined by the border sequences, and intervening DNA is usually inserted into the plant genome as described (Spielmann et al., *Mol. Gen. Genet.,* 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents,* T. Hohn and J. Schell, eds., Springer-Verlag, New York, pp. 179-203 (1985), the entirety of which is herein incorporated by reference. Moreover, recent technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Meth. In Enzymol.,* 153:253-277 (1987), the entirety of which is herein incorporated by reference). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation, and combinations of these treatments. See for example (Potrykus et al., *Mol. Gen. Genet.,* 205:193-200 (1986); Lorz et al., *Mol. Gen. Genet.,* 199:178, (1985); Fromm et al., *Nature,* 319:791, (1986); Uchimiya et al., *Mol. Gen. Genet.:* 204:204, (1986); Callis et al., *Genes and Development,* 1183, (1987); Marcotte et al., *Nature,* 335:454, (1988), all of which the entirety is herein incorporated by reference).

Application of these systems to different plant strains depends upon the ability to regenerate that particular plant strain from protoplasts. Illustrative methods for the regeneration of cereals from protoplasts are described (Fujimura et al., *Plant Tissue Culture Letters,* 2:74, (1985); Toriyama et al., *Theor Appl. Genet.* 205:34. (1986); Yamada et al., *Plant Cell Rep.,* 4:85, (1986); Abdullah et al., *Biotechnology,* 4:1087, (1986), all of which the entirety is herein incorporated by reference).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology,* 6:397, (1988), the entirety of which is herein incorporated by reference). In addition, "particle gun" or high-velocity microprojectile technology can be utilized (Vasil et al., *Bio/Technology* 10:667, (1992), the entirety of which is herein incorporated by reference).

Using the latter technology, DNA is carried through the cell wall and into the cytoplasm on the surface of small metal particles as described (Klein et al., *Nature,* 328:70, (1987); Klein et al., *Proc. Natl. Acad. Sci. USA,* 85:8502-8505, (1988); McCabe et al., *Biotechnology,* 6:923, (1988), all of which the entirety is herein incorporated by reference). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.,* 107:367, (1987); Luo et al., *Plant Mol. Biol. Reporter,* 6:165, (1988), all of which the entirety is herein incorporated by reference), by direct injection of DNA into reproductive organs of a plant (Pena et al., *Nature,* 325:274, (1987), the entirety of which is herein incorporated by reference), or by direct injection of DNA into the cells of immature embryos followed by the rehydration of desiccated embryos (Neuhaus et al., *Theor. Appl. Genet.,* 75:30, (1987), the entirety of which is herein incorporated by reference).

The regeneration, development, and cultivation of plants from single plant protoplast transformants or from various transformed explants is well known in the art (Weissbach and Weissbach, *In: Methods for Plant Molecular Biology*, (Eds.), Academic Press, Inc. San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants, as discussed before. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863, 5,159,135, 5,518,908, all of which the entirety is herein incorporated by reference); soybean (U.S. Pat. Nos. 5,569,834, 5,416,011, McCabe et al., *Biotechnology* 6:923, (1988), Christou et al., *Plant Physiol.*, 87:671-674 (1988), all of which the entirety is herein incorporated by reference); *Brassica* (U.S. Pat. No. 5,463,174, the entirety of which is herein incorporated by reference); peanut (Cheng et al., *Plant Cell Rep.* 15: 653-657 (1996), McKently et al., *Plant Cell Rep.* 14:699-703 (1995), all of which the entirety is herein incorporated by reference); papaya (Yang et al., (1996), the entirety of which is herein incorporated by reference); pea (Grant et al., *Plant Cell Rep.* 15:254-258, (1995), the entirety of which is herein incorporated by reference).

Transformation of monocotyledons using electroporation, particle bombardment, and *Agrobacterium* have also been reported. Transformation and plant regeneration have been achieved in asparagus (Bytebier et al., *Proc. Natl. Acad. Sci. USA* 84:5345, (1987), the entirety of which is herein incorporated by reference); barley (Wan and Lemaux, *Plant Physiol* 104:37, (1994), the entirety of which is herein incorporated by reference); maize (Rhodes et al., *Science* 240: 204, (1988), Gordon-Kamm et al., *Plant Cell,* 2:603, (1990), Fromm et al., *Bio/Technology* 8:833, (1990), Koziel et al., *Bio/Technology* 11:194, (1993), Armstrong et al., *Crop Science* 35:550-557, (1995), all of which the entirety is herein incorporated by reference); oat (Somers et al., *Bio/Technology*, 10:1589, (1992), the entirety of which is herein incorporated by reference); orchardgrass (Horn et al., *Plant Cell Rep.* 7:469, (1988), the entirety of which is herein incorporated by reference); rice (Toriyama et al., *Theor Appl. Genet.* 205:34, (1986); Park et al., *Plant Mol. Biol.*, 32: 1135-1148, (1996); Abedinia et al., *Aust. J. Plant Physiol.* 24:133-141, (1997); Zhang and Wu, *Theor. Appl. Genet.* 76:835, (1988); Zhang et al. *Plant Cell Rep.* 7:379, (1988); Battraw and Hall, *Plant Sci.* 86:191-202, (1992); Christou et al., *Bio/Technology* 9:957, (1991), all of which the entirety is herein incorporated by reference); sugarcane (Bower and Birch, *Plant J.* 2:409, (1992), the entirety of which is herein incorporated by reference); tall fescue (Wang et al., *Bio/Technology* 10:691, (1992), the entirety of which is herein incorporated by reference), and wheat (Vasil et al., *Bio/Technology* 10:667, (1992), the entirety of which is herein incorporated by reference; U.S. Pat. No. 5,631,152, the entirety of which is herein incorporated by reference.

Assays for gene expression based on the transient expression of cloned nucleic acid constructs have been developed by introducing the nucleic acid molecules into plant cells by polyethylene glycol treatment, electroporation, or particle bombardment (Marcotte, et al., *Nature,* 335: 454-457 (1988), the entirety of which is herein incorporated by reference; Marcotte, et al., *Plant Cell,* 1: 523-532 (1989), the entirety of which is herein incorporated by reference; McCarty, et al., *Cell* 66: 895-905 (1991), the entirety of which is herein incorporated by reference; Hattori, et al., *Genes Dev.* 6: 609-618 (1992), the entirety of which is herein incorporated by reference; Goff, et al., *EMBO J.* 9: 2517-2522 (1990), the entirety of which is herein incorporated by reference). Transient expression systems may be used to functionally dissect gene constructs (See generally, Mailga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters enhancers etc. Further any of the nucleic acid molecules of the present invention may be introduced into a plant cell in a manner that allows for over expression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2: 279-289 (1990), the entirety of which is herein incorporated by reference; van der Krol et al., *Plant Cell* 2: 291-299 (1990), the entirety of which is herein incorporated by reference). Cosuppression may result from stable transformation with a single copy nucleic acid molecule that is homologous to a nucleic acid sequence found with the cell (Prolls and Meyer, *Plant J.* 2:465-475 (1992), the entirety of which is herein incorporated by reference) or with multiple copies of a nucleic acid molecule that is homologous to a nucleic acid sequence found with the cell (Mittlesten et al., *Mol. Gen. Genet.* 244: 325-330 (1994), the entirety of which is herein incorporated by reference). Genes, even though different, linked to homologous promoters may result in the cosuppression of the linked genes (Vaucheret, C. R. *Acad. Sci. III* 316: 1471-1483 (1993), the entirety of which is herein incorporated by reference).

This technique has, for example been applied to generate white flowers from red petunia and tomatoes that do not ripen on the vine. Up to 50% of petunia transformants that contained a sense copy of the chalcone synthase (CHS) gene produced white flowers or floral sectors; this was as a result of the post-transcriptional loss of mRNA encoding CHS (Flavell, *Proc. Natl. Acad. Sci.* (*U.S.A.*) 91:3490-3496 (1994)), the entirety of which is herein incorporated by reference). Cosuppression may require the coordinate transcription of the transgene and the endogenous gene, and can be reset by a developmental control mechanism (Jorgensen, *Trends Biotechnol,* 8:340344 (1990), the entirety of which is herein incorporated by reference; Meins and Kunz, In: *Gene Inactivation and Homologous Recombination in Plants* (Paszkowski, J., ed.), pp. 335-348. Kluwer Academic, Netherlands (1994), the entirety of which is herein incorporated by reference).

It is understood that one or more of the nucleic acids of the present invention including those comprising SEQ ID NO:1 through SEQ ID NO:17472 or complement thereof or fragments of either or other nucleic acid molecules of the present invention may be introduced into a plant cell and transcribed using an appropriate promoter with such transcription resulting in the co-suppression of an endogenous protein.

Antisense approaches are a way of preventing or reducing gene function by targeting the genetic material (Mol et al., *FEBS Lett.* 268: 427-430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., *In Genetic Engineering*, Setlow (ed.), Vol. 11, New York: Plenum 49-63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55: 569-597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25: 155-184 (1990), the entirety of which is herein incorporated by reference). An antisense vector is constructed by standard procedures and introduced into cells by transformation, transfection, electroporation, microinjection, or by infection, etc. The type of transformation and choice of vector will determine whether expression is transient or stable. The promoter used for the antisense gene may influence the level, timing, tissue, specificity, or inducibility of the antisense inhibition.

It is understood that protein synthesis activity in a plant cell may be reduced or depressed by growing a transformed plant cell containing a nucleic acid molecule whose non-transcribed strand encodes a protein or fragment thereof.

Antibodies have been expressed in plants (Hiatt et al., *Nature* 342:76-78 (1989), the entirety of which is herein incorporated by reference; Conrad and Fielder, *Plant Mol. Biol.* 26: 1023-1030 (1994), the entirety of which is herein incorporated by reference). Cytoplasmic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16: 4489-4496 (1997), the entirety of which is herein incorporated by reference; Marion-Poll, *Trends in Plant Science* 2: 447-448 (1997), the entirety of which is herein incorporated by reference). For example, expressed anti-abscisic antibodies reportedly result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997), the entirety of which is herein incorporated by reference; Baca et al., *Ann. Rev. Biophys. Biomol. Struct.* 26:461-493 (1997), the entirety of which is herein incorporated by reference). The catalytic abilities of abzymes may be enhanced by site directed mutagensis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585, all of which are herein incorporated in their entirety.

It is understood that any of the antibodies of the present invention may be expressed in plants and that such expression can result in a physiological effect. It is also understood that any of the expressed antibodies may be catalytic.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

The nucleotide sequence provided in SEQ ID NO:1, through SEQ ID NO:17472 or fragment thereof, or complement thereof, or a nucleotide sequence at least 90% identical, preferably 95%, identical even more preferably 99% or 100% identical to the sequence provided in SEQ ID NO:1 through SEQ ID NO:17472 or fragment thereof, or complement thereof, can be "provided" in a variety of mediums to facilitate use fragment thereof. Such a medium can also provide a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410 (1990)) and BLAZE (Brutlag et al., *Comp. Chem.* 17:203-207 (1993), the entirety of which is herein incorporated by reference) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTN and BLASTX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences or sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used as the search means for the computer-based systems of the present invention. Having now generally described the invention, the same will be more readily understood through reference to the following examples which are provided by way of illustration, and are not intended to be limiting of the present invention, unless specified.

EXAMPLE 1

The cDNA library LIB3179 is generated from maize (DK604, Dekalb Genetics, Dekalb, Ill. U.S.A.) jasmonic acid treated leaf tissue from plants at the V4 to V6 plant development stage. Seeds are planted in 4 inch pots containing Metro 200 growing medium on greenhouse tables. Plants are watered when found to be dry (about every 48 hours). NPK 2199 fertilizer is applied once per week. The plants are grown in a greenhouse in 15 hr day/9 hr night cycles. The daytime temperature is approximately 85° F. and the nighttime temperature is approximately 65° F. The light intensity is about 600 microEinsteins. At the V4 to V6 plant development stage, plant leaves are sprayed with a jasmonic acid (Sigma J-2500, Sigma, St. Louis, Mo. U.S.A.) solution (1 mg/ml) in 0.1% Tween-20. Plants are sprayed until runoff. Jasmonic acid treated leaf tissues are collected from plants at 18, 24, and 48 hours after jasmonic acid treatment. Equal weight of leaf tissues from the three timepoints is pooled and frozen immediately in liquid nitrogen. The harvested leaf tissue is stored at −80° C. until RNA preparation. The RNA is purified from the stored tissue and the cDNA library is constructed as described in Example 2.

The subtractive cDNA library LIB3227 is generated by subtracting driver cDNA, which is prepared from leaf and root tissues harvested from maize (H99, USDA Maize Genetic Stock Center, Urbana, Ill. U.S.A.) plants, from target cDNA, which is prepared from maize (H99) immature ear tissue from 8 weeks old plants. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Ears are harvested from 8 week old plants and are approximately 3.5-4.5 cm long. Kernels are dissected away from the cob, frozen in liquid nitrogen and stored at −80 C until preparation of RNA. The RNA is purified from the stored tissue and the subtractive cDNA library is constructed as described in Example 2.

The subtractive cDNA library LIB3228 is generated by subtracting driver cDNA, which is prepared from leaf and root tissues harvested from maize (H99, USDA Maize Genetic Stock Center, Urbana, Ill. U.S.A.) plants, from target cDNA, which is prepared from maize (H99) microspore tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature anthers from 7 week old tassels. The immature anthers are first dissected from the 7 week old tassel with a scalpel on a glass slide covered with water. The microspores (immature pollen) are released into the water and are recovered by centrifugation. The microspore suspension is immediately frozen in liquid nitrogen. The harvested tissue is then stored at −80° C. until RNA preparation. The RNA is purified from the stored tissue and the subtractive cDNA library is constructed as described in Example 2.

The cDNA library LIB3279 is generated from maize (H99, USDA Maize Genetic Stock Center, Urbana, Ill. U.S.A.) anther tissue from 1-2 cm tassels harvested from plants 37 days after germination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected at about 37 days after germination. At this stage, the anthers are green, 1 to 2 cm long, and enclosed in staminate spikelets. The developing anthers are dissected away from the plants and immediately frozen in liquid nitrogen. The harvested tissue is then stored at −80° C. until RNA preparation. The RNA is purified from the stored tissue and the cDNA library is constructed as described in Example 2.

EXAMPLE 2

The total RNA is purified using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. cDNA libraries are prepared using the Superscript™ Plasmid System for cDNA synthesis and Plasmid Cloning (Gibco BRL, Life Technologies, Gaithersburg, Md. U.S.A.), as described in the Superscript II cDNA library synthesis protocol. The cDNA libraries are quality controlled for a good insert:vector ratio.

Target cDNA library is generated as described above from the target tissues described in Example 1. Once a library of satisfactory construction has been made, 106 colony forming units are grown in a large culture and then plasmid target cDNA is isolated for library subtraction. The poly A region of the target plasmid cDNA is blocked with poly T, which is generated using Not I-oligo dT primer following standard PCR procedures.

Driver cDNA is prepared from mRNA isolated from leaf and root tissues and driver first strand cDNA is covalently linked to Dynabeads, following a protocol similar to that described in the Dynal literature. The single strand driver cDNA is then stored on ice until subtraction.

For subtraction, the mixture of the target plasmid cDNA and poly T is heat denatured for 4 minutes at 94° C., immediately placed on ice for 2 minutes, and then mixed with driver cDNA-dynabeads in about 400 μl of 4×SSPE solution. The hybridization solution is heated for 1 minute at 94° C. prior to hybridization at 68° C. for 20 hours. The driver is trapped with a magnetic holder and the hybridization solution is removed from the system for the next round of hybridization with the refreshed driver cDNA-Dynabeads. The driver cDNA-Dynabeads is refreshed by heat denaturation at 94° C. in distilled water for 4 minutes, followed by trapping with a magnetic holder. The water containing the eluted plasmids is removed. The driver cDNA-Dynabeads is then resuspended in the previously removed hybridization solution for a second round of hybridization. This process is repeated a third time. After the third hybridization, the remaining unsubtracted plasmid is concentrated from the hybridization solution by filtration and used to transform *E. coli*.

EXAMPLE 3

The cDNA libraries are plated on LB agar containing the appropriate antibiotics for selection and incubated at 37° for a sufficient time to allow the growth of individual colonies. Single colonies are individually placed in each well of a 96-well microtiter plates containing LB liquid including the selective antibiotics. The plates are incubated overnight at approximately 37° C. with gentle shaking to promote growth of the cultures. The plasmid DNA is isolated from each clone using Qiaprep plasmid isolation kits, using the conditions recommended by the manufacturer (Qiagen Inc., Santa Clara, Calif. U.S.A.).

The template plasmid DNA clones are used for subsequent sequencing. For sequencing the cDNA libraries LIB3179, LIB3227, LIB3228, and LIB3279, a commercially available sequencing kit, such as the ABI PRISM dRhodamine Terminator Cycle Sequencing Ready Reaction Kit with AmpliTaq® DNA Polymerase, FS, is used under the conditions recommended by the manufacturer (PE Applied Biosystems, Foster City, Calif.). The ESTs of the present invention are generated by sequencing initiated from the 5' end of each cDNA clone.

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, N.Y., the entirety of which is herein incorporated by reference).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07572902B2). An electronic copy of the "Sequence Listing" will also be available from the USPTO upon request and payment of the fee set forth in 37 CFR 1.19(b)(3).

We claim:

1. A substantially purified nucleic acid molecule comprising a nucleic acid sequence, wherein said nucleic acid sequence shares between 100% and 90% sequence identity to the nucleic acid sequence of SEQ ID NO: 16372 or the complement thereof.

2. The substantially purified nucleic acid molecule of claim 1, wherein said nucleic acid molecule encodes a maize protein or fragment thereof.

3. The substantially purified nucleic acid molecule of claim 1, wherein said nucleic acid sequence shares between 100% and 95% sequence identity with the nucleic acid sequence of SEQ ID NO: 16372 or the complement thereof.

4. The substantially purified nucleic acid molecule of claim 3, wherein said nucleic acid sequence shares between 100% and 98% sequence identity with the nucleic acid sequence of SEQ ID NO: 16372 or the complement thereof.

5. The substantially purified nucleic acid molecule of claim 4, wherein said nucleic acid sequence shares between 100% and 99% sequence identity with the nucleic acid sequence of SEQ ID NO: 16372 or the complement thereof.

6. The substantially purified nucleic acid molecule of claim 5, wherein said nucleic acid sequence shares 100% sequence identity with the nucleic acid sequence of SEQ ID NO: 16372 or the complement thereof.

7. A transformed plant having a nucleic acid molecule which compnses:
   (a) an exogenous promoter region which functions in a plant cell to cause the production of an mRNA molecule, which is linked to;
   (b) a structural nucleic acid molecule, wherein said structural nucleic acid molecule comprises a nucleic acid sequence, wherein said nucleic acid sequence shares between 100% and 90% sequence identity to the nucleic acid sequence of SEQ ID NO: 16372 or the complement thereof,
   which is linked to
   (c) a 3' non-translated sequence that functions in said plant cell to cause the termination of transcription and the addition of polyadenylated ribonucleotides to said 3' end of said mRNA molecule.

8. The transformed plant according to claim 7, wherein said nucleic acid sequence is the complement of the nucleic acid sequence of SEQ ID NO: 16372.

9. The transformed plant according to claim 7, wherein said plant is selected from the group consisting of soybean, maize, cotton and wheat.

10. A transformed seed comprising a transformed plant cell comprising a nucleic acid molecule which comprises:
   (a) an exogenous promoter region which functions in said plant cell to cause the production of an mRNA molecule, which is linked to;
   (b) a structural nucleic acid molecule, wherein said structural nucleic acid molecule comprises a nucleic acid sequence, wherein said nucleic acid sequence shares between 100% and 90% sequence identity to the nucleic acid sequence of SEQ ID NO: 16372 or the complement thereof,
   which is linked to
   (c) a 3' non-translated sequence that functions in said plant cell to cause the termination of transcription and the addition of polyadenylated ribonucleotides to said 3' end of said mRNA molecule.

11. The transformed seed according to claim 10, wherein said nucleic acid sequence is the complement of the nucleic acid sequence of SEQ ID NO: 16372.

12. The transformed seed according to claim 10, wherein said seed is selected from the group consisting of soybean, maize, cotton and wheat seed.

13. The transformed seed according to claim 10, wherein said exogenous promoter region functions in a seed cell.

14. The transformed seed according to claim 10, wherein said exogenous promoter region functions in a leaf cell.

15. A method of producing a genetically transformed plant, comprising the steps of:
  (a) inserting into the genome of a plant cell a recombinant, double-stranded DNA molecule comprising
    (i) a promoter which functions in plant cells to cause the production of an RNA sequence,
    (ii) a structural nucleic acid molecule, wherein said structural nucleic acid molecule comprises a nucleic acid sequence, wherein said nucleic acid sequence shares between 100% and 90% sequence identity to the nucleic acid sequence of SEQ ID NO: 16372 or the complement thereof,
  which is linked to
    (iii) a 3' non-translated sequence which functions in plant cells to cause the addition of polyadenylated nucleotides to the 3' end of an RNA sequence,
  (b) obtaining a transformed plant cell with said structural nucleic acid molecule that encodes one or more proteins, wherein said structural nucleic acid molecule is transcribed and results in expression of said protein(s); and
  (c) regenerating from said transformed plant cell a genetically transformed plant.

16. A method for reducing expression of a protein in a plant cell comprising growing a transformed plant cell containing a nucleic acid molecule wherein the non-transcribed strand of said nucleic acid molecule encodes a protein or fragment thereof, and wherein the transcribed strand of said nucleic acid molecule is complementary to a nucleic acid molecule comprising the nucleic acid sequence of SEQ ID NO: 16372 or the complement thereof, and whereby said transcribed strand reduces or depresses expression of said protein.

17. A method for increasing expression of a protein in a plant cell comprising growing a transformed plant cell containing a nucleic acid molecule that encodes a protein or fragment thereof, wherein said nucleic acid molecule comprises the nucleic acid sequence of SEQ ID NO: 16372 or the complement thereof and whereby said nucleic acid molecule increases expression of said protein.

18. A method of producing a plant containing reduced levels of a protein comprising:
  (a) transforming a plant cell with a nucleic acid molecule comprising the nucleic acid sequence of SEQ ID NO: 16372 or the complement thereof, wherein said nucleic acid molecule is transcribed and results in co-suppression of endogenous protein synthesis activity, and
  (b) regenerating said plant comprising said plant cell and producing subsequent progeny from said plant.

19. A method of growing a transgenic plant comprising
  (a) planting a transformed seed comprising the nucleic acid sequence of SEQ ID NO: 16372 or the complement thereof, and
  (b) growing a plant from said seed.

* * * * *

UNITED STATES PATENT AND TRADEMARK OFFICE
CERTIFICATE OF CORRECTION

PATENT NO. : 7,572,902 B2 Page 1 of 1
APPLICATION NO. : 11/330364
DATED : August 11, 2009
INVENTOR(S) : Abad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 586 days.

Signed and Sealed this

Seventh Day of September, 2010

David J. Kappos
*Director of the United States Patent and Trademark Office*